(12) United States Patent
Zhou et al.

(10) Patent No.: US 9,151,701 B2
(45) Date of Patent: Oct. 6, 2015

(54) MICROFLUIDIC SYSTEMS

(71) Applicant: RHEONIX, INC., Ithaca, NY (US)

(72) Inventors: Peng Zhou, Newtown, PA (US); Lincoln C. Young, Ithaca, NY (US)

(73) Assignee: RHEONIX, INC., Ithaca, NY (US)

( * ) Notice: Subject to any disclaimer, the term of this patent is extended or adjusted under 35 U.S.C. 154(b) by 37 days.

(21) Appl. No.: 14/103,008

(22) Filed: Dec. 11, 2013

(65) Prior Publication Data
US 2014/0093431 A1    Apr. 3, 2014

Related U.S. Application Data

(63) Continuation of application No. 11/594,444, filed on Nov. 8, 2006, now Pat. No. 7,976,795.

(60) Provisional application No. 60/760,552, filed on Jan. 19, 2006.

(51) Int. Cl.
*B01L 3/00* (2006.01)
*F04B 19/00* (2006.01)
(Continued)

(52) U.S. Cl.
CPC .............. *G01N 1/28* (2013.01); *B01L 3/5025* (2013.01); *B01L 3/50273* (2013.01); *B01L 3/502715* (2013.01); *B01L 3/502738* (2013.01); *F04B 43/043* (2013.01); *F16K 99/0001* (2013.01); *F16K 99/0015* (2013.01); *F16K 99/0059* (2013.01); *B01L 7/00* (2013.01); *B01L 2200/026* (2013.01); *B01L 2200/027* (2013.01); *B01L 2200/028* (2013.01); *B01L 2200/04* (2013.01); *B01L 2200/0621* (2013.01); *B01L 2200/0684* (2013.01); *B01L 2200/10* (2013.01); *B01L 2200/16* (2013.01); *B01L 2300/0654* (2013.01); *B01L 2300/0816* (2013.01); *B01L 2300/0864* (2013.01); *B01L 2300/0867* (2013.01); *B01L 2300/0874* (2013.01); *B01L 2300/0887* (2013.01); *B01L 2300/1827* (2013.01); *B01L 2400/0481* (2013.01); *B01L 2400/0622* (2013.01); *B01L 2400/0633* (2013.01); *B01L 2400/0655* (2013.01);
(Continued)

(58) Field of Classification Search
CPC .............. B01L 2300/0816; B01L 2400/084; B01L 2300/0867; B01L 2300/0887; B01L 2300/0861; B01L 2200/027; B01L 3/502715; B01L 2200/028; B01L 2300/0874; B01L 2200/10; B01L 2300/0654; B01L 2200/16; B01L 2300/0864; B01L 2400/0622; B01L 2400/0666; B01L 3/5025; B01L 2200/026; B01L 2400/0487; B01L 2400/0638; B01L 2200/025; B01L 9/527; B01L 2300/185; B01L 3/527; G01N 30/6095; G01N 2030/8881; G01N 30/6047; G01N 30/74; G01N 35/1002; B81B 2201/036
USPC .................................. 422/500–505; 436/180
See application file for complete search history.

(56) References Cited

U.S. PATENT DOCUMENTS

| | | | | |
|---|---|---|---|---|
| 5,062,942 | A | * 11/1991 | Kambara et al. | 204/612 |
| 2005/0027184 | A1 | * 2/2005 | Saldivar et al. | 600/368 |
| 2005/0214173 | A1 | * 9/2005 | Facer et al. | 422/100 |

*Primary Examiner* — Dean Kwak
(74) *Attorney, Agent, or Firm* — William Greener; Bond, Schoeneck & King, PLLC

(57) ABSTRACT

The systems and methods disclosed herein include a microfluidic system, comprising a pneumatic manifold having a plurality of apertures, and a chip manifold having channels disposed therein for routing pneumatic signals from respective ones of the apertures to a plurality of valves in a microfluidic chip, wherein the channels route the pneumatic signals in accordance with a configuration of the plurality of valves in the microfluidic chip.

24 Claims, 18 Drawing Sheets

(51) Int. Cl.
*G01N 1/10* (2006.01)
*G01N 1/28* (2006.01)
*F04B 43/04* (2006.01)
*F16K 99/00* (2006.01)
*B01L 7/00* (2006.01)

(52) U.S. Cl.
CPC ... *B01L 2400/0666* (2013.01); *B01L 2400/084* (2013.01); *F16K 2099/0084* (2013.01); *F16K 2099/0094* (2013.01); *Y10T 137/0324* (2015.04); *Y10T 436/117497* (2015.01); *Y10T 436/2575* (2015.01)

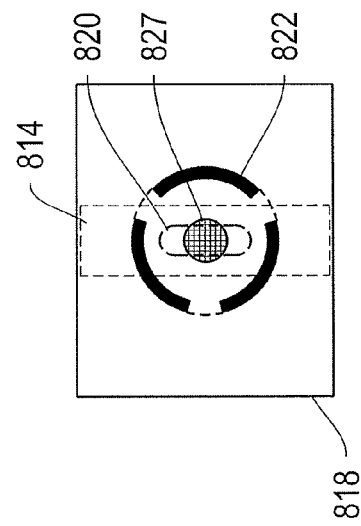
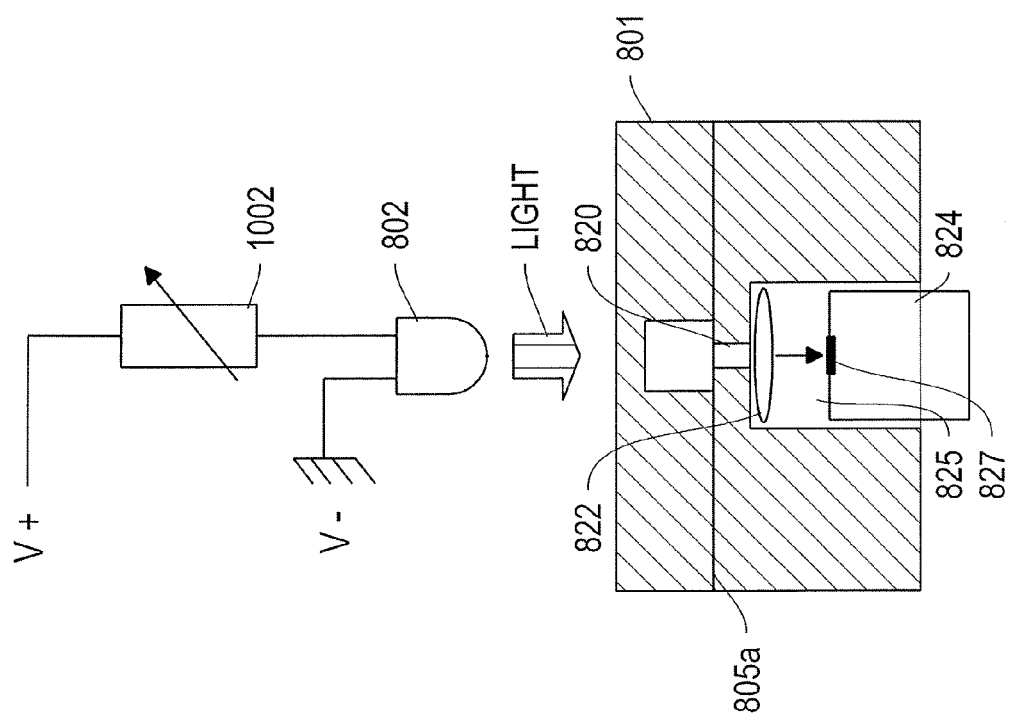
Figure 13
Figure 12

MICROFLUIDIC SYSTEMS

CROSS-REFERENCE TO RELATED APPLICATIONS

This application is a continuing (CONTINUATION) application of U.S. Ser. No. 11/594,444 filed on Nov. 8, 2006, which claims priority to Provisional Application No. 60/760,552, filed on Jan. 19, 2006, the subject matters of which are incorporated herein by reference in their entireties.

BACKGROUND

"Microfluidics" generally refers to systems, devices, and methods for processing small volumes of fluids. Because microfluidic systems can process a wide variety of fluids, such as chemical or biological samples, these systems have many application areas, such as biochemical assays (for, e.g., medical diagnoses), biochemical sensors, or life science research in general.

One type of microfluidic device is a microfluidic chip. Microfluidic chips may include micro-scale features (or "microfeatures"), such as channels, valves, pumps, and/or reservoirs for storing fluids, for routing fluids to and from various locations on the chip, and/or for reacting fluidic reagents. In some cases, microfluidic chips may include more complex micro-scale structures such as mixing devices or sensors for performing other processing functions on the fluids. A microfluidic chip that integrates various microfeatures to provide various fluid processing functions is sometimes called a "Lab-on-a-chip."

However, many existing microfluidic devices are prohibitively expensive or prohibitively difficult to operate to be suitable for many applications. For example, many existing systems are too expensive to be disposable or do not have enough programmed automation to be operated by an untrained field technician. Therefore, these systems cannot be used in certain non-laboratory environments. Moreover, many microfluidic systems are built for one specific application, and cannot be adapted or customized for other applications. Many microfluidic systems are not modular, and therefore cannot benefit from the efficiencies of mass-production or allow a user to reconfigure easily the system for various applications at hand.

Moreover, existing microfluidic systems lack adequate detection and analysis systems. While microfluidic devices deliver higher process speeds and require only small volumes of sample, these small volumes of samples are difficult to detect and analyze. By way of comparison, an exemplary non-microfluidic implementation is an Enzyme Linked Immunosorbent Assay (ELISA), using a 96 well microplate with a well diameter of 6 mm for the sample cuvet. In this case, the final volume for a spectrometer measurement is around 100 µl and corresponds to an optical path length for an optical detector of about 4 mm. In contrast, a typical microfluidic channel or reservoir may have a channel depth of less than about 100 microns. This optical path length is thus about 40-fold lower than for a conventional microplate assay, which can correspond to a 40-fold decrease in detection signal intensity.

Furthermore, many existing detection systems do not adequately integrate to a microfluidic chip. As a result, an untrained technician may have difficulty interfacing the microfluidic chip to the detector in order to provide meaningful results. Finally, many existing systems use expensive optical components.

Thus, there exists a need for improved microfluidic systems for processing fluids, such as biological or chemical samples. It is desired that the systems are inexpensive and preferably disposable. It is desired that the systems be simple to operate and that many or substantially all of the fluid processing steps be automated. It is desired that the systems be customizable, and be modular such that the system can be easily and rapidly reconfigured to suit various applications. It is desired that the systems include integrated detection systems which provide high detection sensitivity, but are inexpensive and preferably disposable.

SUMMARY

This invention, in various embodiments, addresses deficiencies in the prior art by providing microfluidic devices, systems, and methods. The systems and methods described herein include plastic microfluidic chips that route and process one or more reagents, along with manifold structures, controllers, and computers. Additionally, the systems and methods include detectors and sensors for analyzing fluidic reagents after they have reacted.

More particularly, microfluidic chips described herein include various micro-scale features ("microfeatures") such as valves, pumps, channels, and reservoirs. These microfeatures are interconnected and allow for various combinations of fluid flow patterns that can be user specified and tailored to a specific application. In some implementations, the chip couples to a reagent cartridge or separate microfluidic reagent chip having reagent reservoirs. The chip's microfeatures transport one or more reagents from respective reagent reservoirs, react the reagents, and transport the reaction products to outlet reservoirs. Detectors then analyze the reaction products.

Certain microfeatures on the chip, such as pumps and valves, are actively actuated by an external stimulus and thus may be referred to as "active" components. For example, in some implementations the pumps and valves are pneumatically actuated. In certain implementations, a user specifies a desired fluid flow pattern on the chip. In order to pneumatically actuate the pumps and valves to produce the desired fluid flow pattern, the systems include a chip manifold for routing pneumatic signals to appropriate pumps and valves, a pneumatic manifold having pneumatic transducers coupled thereto for providing the pneumatic signals to the chip manifold, a controller for actuating the pneumatic transducers according to programmed logic instructions, and a computer for interfacing the controller and the user.

In one feature, the above-described systems are modular; they include a pneumatic manifold that provides pneumatic signals and a separate chip manifold that routes the pneumatic signals to appropriate pumps and valves on the chip. This modular approach results in a reconfigurable and customizable system. More particularly, various applications may call for various respective microfluidic chips. The systems described herein allow a user to use a single computer, controller, and pneumatic manifold for any of the various microfluidic chips, and the user need only couple the pneumatic manifold to a chip manifold specific to a particular chip at hand.

The invention also includes systems and methods for detecting, analyzing, and characterizing fluids. For example, systems described herein include optical detector systems that measure the concentration of an analyte in a fluidic sample. The optical detector systems can measure the concentration of several fluidic samples in parallel, and can operate with high detection sensitivities in uncontrolled environments.

In one aspect, the above-described systems are inexpensive and may be disposable. In certain embodiments, the microfluidic chips and manifolds of this invention are made entirely from inexpensive plastic materials. In one embodiment, an entire microfluidic system that is suitable for portable immunoassay, including a chip, associated manifolds, and reagent cartridges or reagent chips, is made from polystyrene, which results in extremely low fabrication costs.

While certain fabrication methods may damage or distort microfeatures formed within plastics, in certain implementations this invention uses weak-solvent bonding (e.g., acetonitrile solvent lamination methods). Weak-solvent bonding preserves the integrity and reliability of the microfeatures disposed within the chips and manifolds. These aspects of the technology are described in U.S. patent application Ser. No. 11/242,694, incorporated herein by reference in its entirety. Additionally, other aspects of the present invention can be used alone, or in combination with aspects of the inventions described in U.S. patent application Ser. No. 11/242,694.

Moreover, in certain embodiments the invention uses inexpensive but effective equipment in place of other more expensive equipment known in the art. For example, the invention uses inexpensive and disposable optical detection systems in place of more complex and expensive equipment used in commercial implementations.

In another aspect, the above-described systems are automated. A programmable controller automatically drives solenoids, which transmit pneumatic signals through manifold structures. The manifold structures route the signals, which then actuate pumps and valves to transport fluid on the chip. By actuating the pumps and valves on the chip in specific sequences, a user can efficiently perform a large number of assays unattended.

Because the devices may have small dimensions, may be disposable, may be customizable and reconfigurable, and may be automated, they provide a framework for offering inexpensive portable "Point-of-Care" (POC) systems with automated assay processing that can be run by users with little training.

In one aspect, the invention includes a microfluidic system, comprising a pneumatic manifold having a plurality of apertures, and a chip manifold having channels disposed therein for routing pneumatic signals from respective ones of the apertures to a plurality of valves in a microfluidic chip, wherein the channels route the pneumatic signals in accordance with a configuration of the plurality of valves in the microfluidic chip.

In one configuration, the chip manifold includes at least one set of channels for routing a pneumatic signal from one aperture of the pneumatic manifold to a plurality of the valves in the microfluidic chip. The at least one set of channels may comprise a single channel for routing the pneumatic signal from the aperture to a plurality of channels branching from the single channel, wherein the plurality of channels branching from the single channel route the pneumatic signal to respective ones of the plurality of valves. Additionally or alternatively, the at least one set of channels may include a set of channels consisting of a single channel.

In one feature, the invention may include a plurality of microfluidic chips having different respective configurations of valves, and respective chip manifolds corresponding to the plurality of microfluidic chips, wherein the respective chip manifolds have channels disposed therein for routing pneumatic signals from at least some of the apertures of the pneumatic manifold to at least some of the valves on corresponding ones of the associated plurality of microfluidic chips, and the channels of the respective chip manifolds route the pneumatic signals in accordance with the respective configurations of the plurality of microfluidic chips.

In another feature, the systems may include a controller for controlling the pneumatic signals being transmitted through the plurality of apertures.

In one configuration, the plurality of apertures have respective pneumatic transducers that fluidly couple to the plurality of apertures for transmitting the pneumatic signals through the plurality of apertures, and the controller may be adapted to transmit electronic signals that individually actuate the respective pneumatic transducers in a sequence according to logic instructions from the controller. In certain configurations, the pneumatic transducers comprise solenoids.

According to one feature, at least one of the pneumatic transducers may include an output port for transmitting a pneumatic pressure, and a switch for selecting the pneumatic pressure as one of a positive pressure and a negative pressure, wherein the selecting is based on at least one of the electronic signals. The pneumatic pressure supplied to the output port may be generated by a DC-powered diaphragm pump that is designed to enhance the portability of the microfluidic system. The pneumatic manifold may further comprise attachment ports for coupling pneumatic transducers to the pneumatic manifold. The pneumatic manifold may include a plurality of laminated layers.

According to one configuration, the plurality of apertures have respective pneumatic transducers that fluidly couple to the plurality of apertures, the pneumatic manifold includes at least one positive pressure source and at least one negative pressure source, and the at least one positive pressure source and the at least one negative pressure source fluidly couple to the pneumatic transducers. The at least one positive pressure source may provide signals corresponding to a first state of binary logic communicated to the pneumatic transducers from a controller, and the at least one negative pressure source may provide signals corresponding to a second state of binary logic communicated from a controller to the pneumatic transducers.

In one feature, the microfluidic chip includes microfluidic pumps, and each of the microfluidic pumps has three or more of the plurality of valves. The microfluidic chip may include a plurality of fluidic channels for transporting and reacting fluidic reagents. The microfluidic chip may include reagent reservoirs for storing fluidic reagents, and outlet reservoirs for storing reaction products of the fluidic reagents.

According to another feature, the microfluidic system may comprise an optical detection system for analyzing fluidic samples in the microfluidic chip. The optical measurement system may include a light source for transmitting light through the fluidic reagent, and a transducer for receiving at least a portion of the transmitted light and producing an electronic signal related to the strength of the received portion of the transmitted light. The optical detection system may further include a slit disposed between the light source and the transducer for attenuating ambient light. The optical detection system may include a band-pass filter disposed between the light source and the transducer.

In certain configurations, each of the pneumatic manifold, the chip manifold, and the microfluidic chip comprises a non-elastomer plastic material. The non-elastomer plastic material may comprise at least one of polymethyl methacrylate, polystyrene, polycarbonate, and acrylic.

In one aspect, the invention includes a method of operating a microfluidic system, comprising transmitting, by a pneumatic manifold, pneumatic signals to a chip manifold, routing, by the chip manifold, the pneumatic signals to a plurality of valves in a microfluidic chip, and actuating, by the pneumatic signals, the valves in the microfluidic chip to transport fluid through the microfluidic chip.

In certain implementations, the methods described herein may also comprise routing a pneumatic signal from one aperture of the pneumatic manifold to a plurality of valves in the microfluidic chip.

In certain implementations, the methods may include activating, by a programmable controller, the sequence of pneumatic signals. The methods may include programming the controller with program logic instructions.

In certain implementations, the methods may include transmitting the pneumatic signals by switching, by a pneumatic transducer, between a positive pressure output and a negative pressure output in accordance with the program logic instructions. Activating the sequence of pneumatic signals may comprise transmitting electronic signals to pneumatic transducers coupled to the pneumatic manifold, thereby actuating the pneumatic transducers.

In certain implementations, the methods may comprise transporting and reacting fluidic reagents in the microfluidic chip.

In one feature, the methods may include characterizing fluidic samples in the microfluidic chip with an optical detection system. Characterizing the fluidic samples may comprise transmitting light through the fluidic samples and detecting the amount of light allowed to pass through the fluidic samples. Characterizing the fluidic samples may further comprise filtering ambient light.

In another aspect, the invention includes a microfluidic system, comprising an array of pneumatic transducers, and a chip manifold having channels disposed therein for routing pneumatic signals from respective ones of the pneumatic transducers to a plurality of valves in a microfluidic chip, wherein the channels route the pneumatic signals in accordance with a configuration of the plurality of valves in the chip.

The fluids described herein may comprise a liquid, a gas, a solid that is substantially dissolved in a fluid material, a slurry material, an emulsion material, or a fluid material with particles suspended therein. "Reagents" generally refer to any materials, such as fluids, that react to produce a reaction product. As used herein, a "pneumatic signal" generally refers to any sequence of air pressures, and a pneumatic transducer refers to any device that produces a pneumatic signal based on an input, such as an electrical signal input.

BRIEF DESCRIPTION OF THE DRAWINGS

These and other features and advantages will be more fully understood by the following illustrative description with reference to the appended drawings, in which like elements are labeled with like reference designations, and in which the drawings may not be drawn to scale.

FIGS. 7A-D show a solenoid, according to an illustrative embodiment of the invention.

FIG. 12 shows a close-up front view of the detection components associated with one exemplary detecting window, according to an illustrative embodiment of the invention.

FIG. 13 shows a top view of the detection components associated with the exemplary detecting window of FIG. 12.

DETAILED DESCRIPTION OF ILLUSTRATIVE EMBODIMENTS

The invention, in various embodiments, provides microfluidic devices, systems, and methods. The following detailed description of the invention refers to the accompanying drawings. The following detailed description does not limit the invention. Instead, the scope of the invention is at least the scope defined by the appended claims and equivalents.

Figure 1A:
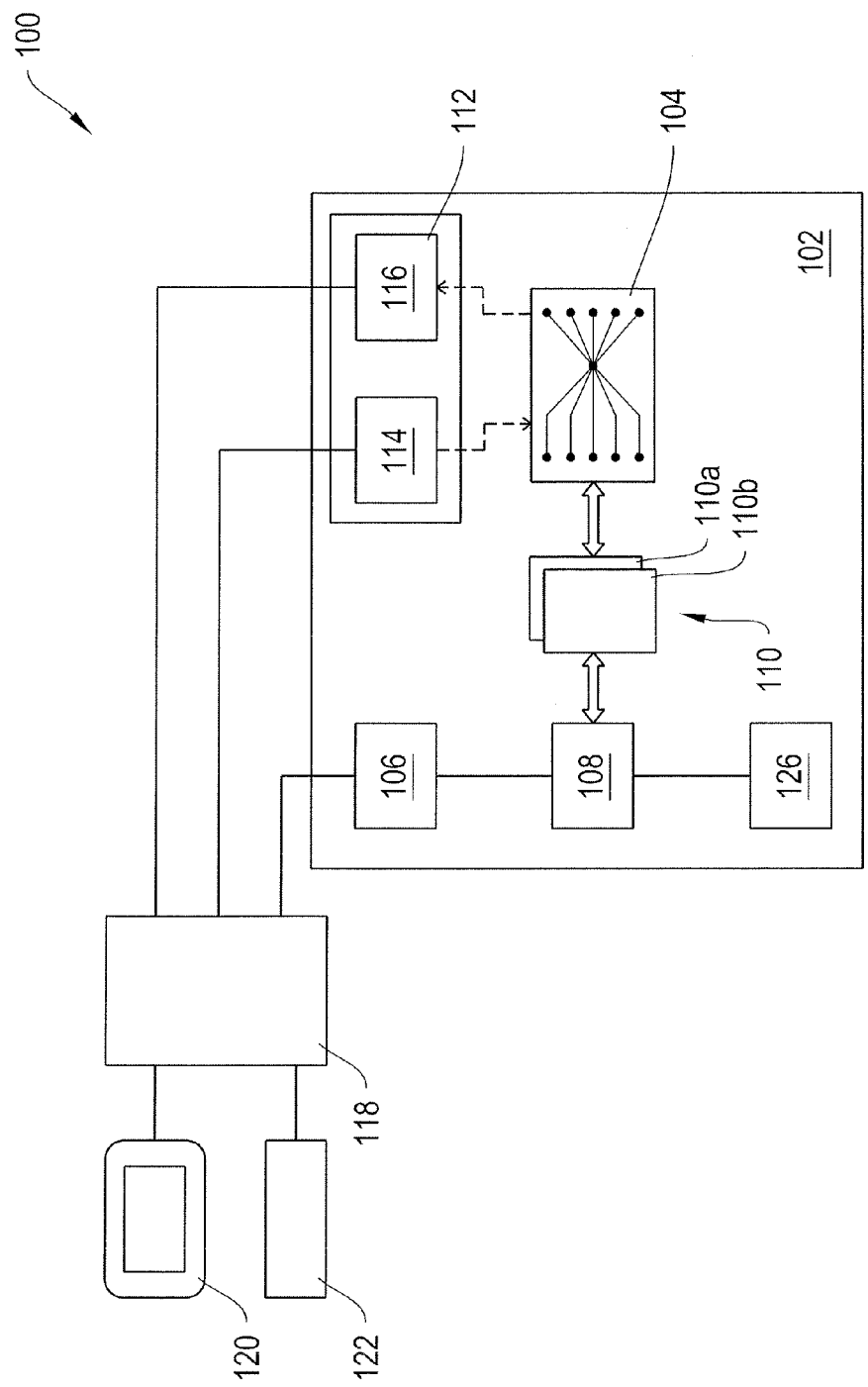
FIG. 1A shows a schematic of a microfluidic system, according to an illustrative embodiment of the invention.

FIG. 1A shows a schematic of a microfluidic system 100, according to an illustrative embodiment of the invention. The microfluidic system 100 includes a microfluidic assay system 102, a computer 118, a computer display 120, and an input device 122.

The microfluidic system 100 includes a microfluidic chip 104. The microfluidic chip 104 includes microfeatures such as channels, valves, pumps, and/or reservoirs for storing fluids, for routing fluids to and from various locations on the chip, and/or for reacting fluidic reagents. In order to route fluids through channels of the chip according to desired fluid flow patterns, the valves and pumps are pneumatically actuated in a certain sequence in accordance with the desired fluid flow pattern.

The pneumatic signals that actuate the pumps and valves are generated by an array of pneumatic transducers 108, which couples to the chip 104 via manifold structures 110. In the depicted embodiment, the array of pneumatic transducers is a solenoid array 108. The manifold structures 110 include a pneumatic manifold 110a, which includes apertures for transmitting pneumatic signals therethrough, and a chip manifold 110b, for routing the pneumatic signals to appropriate pumps and valves on the chip 104. The microfluidic chip 104, the manifold structures 110, and the solenoid array 108 will be described in more detail below.

The microfluidic assay system 102 also includes a diaphragm pump 126 that supplies a positive or negative pressure to the solenoids in the solenoid array 108. In addition, a controller 106 of the microfluidic assay system 102 controls the pneumatic signals generated by the solenoids in the solenoid array 108, and thereby controls the resulting fluid flow pattern on the chip 104. The computer 118 transmits commands and/or programs to the controller 106. The input device 122 and the display 120 interface the computer 118 and a user (not shown). The input device 122, the display 120, the computer 118, the controller 106 and the diaphragm pump 126 will be described in more detail below.

The microfluidic assay system 102 also includes an optical detection system 112 having a light source 114 and a detector 116 that analyze fluids on the microfluidic chip 104 (e.g., to analyze reaction products) using optical detection techniques. The optical detection system 112 will be discussed in more detail below.

Figure 1B:
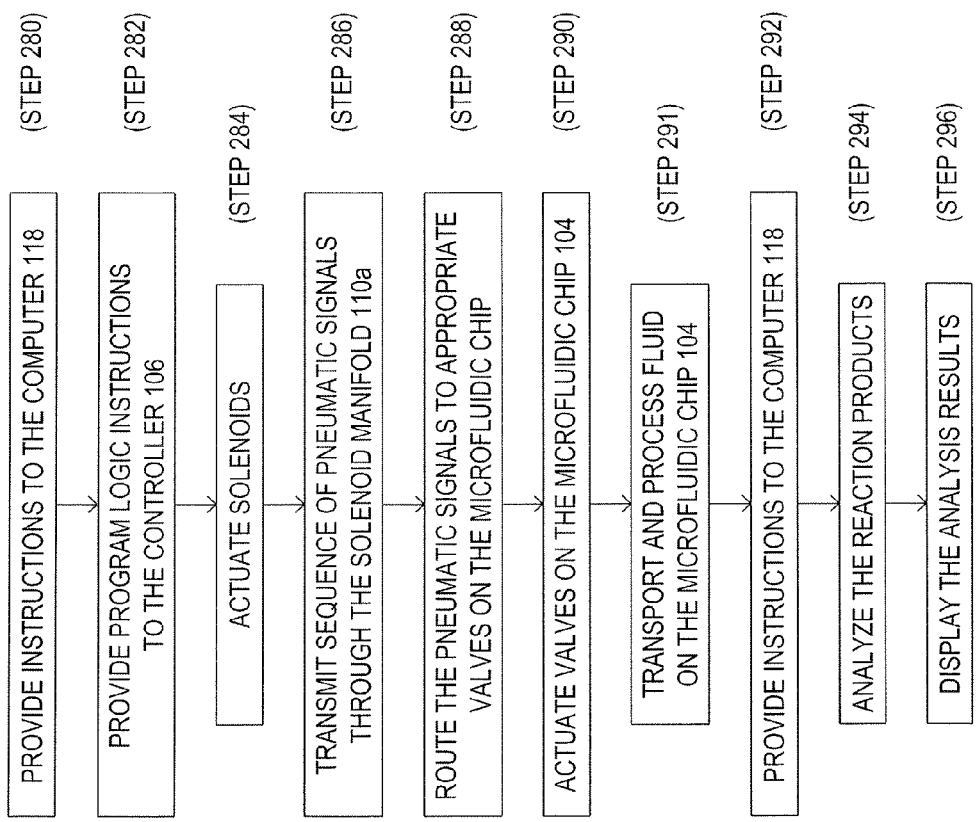
FIG. 1B illustrates a method of operation of the microfluidic system of FIG. 1A, according to an exemplary use of the invention.

FIG. 1B illustrates a method of operation of the system 200, according to an illustrative embodiment of the invention. In use, a user first interfaces with the computer 118 via the input device 122 and the display 120. The user provides instructions to the computer 118 (step 280) related to the fluid processing functions (e.g., the reactions among reagents) that will take place on the chip 104. Next, the computer 118 provides program logic instructions to the controller 106 (step 282). However, in other exemplary methods the controller 106 is pre-programmed with logic instructions, as will be discussed in more detail below. The controller 106 then transmits electronic signals to the solenoids in the solenoid array 108 to actuate the solenoids in sequences dictated by the program logic instructions (step 284). The solenoids, when actuated, transmit a sequence of pneumatic signals through the pneumatic manifold 110a to the chip manifold 110b (step 286). The chip manifold 110b includes channels that route the pneumatic signals to appropriate valves on the microfluidic chip (step 288). The pneumatic signals then actuate the valves on the microfluidic chip 104 (step 290), which transport and process fluid on the microfluidic chip 104 (step 291) in accordance with the user's instructions to the computer 118.

In certain implementations, as mentioned above, the fluids are sample, and in some cases may be reagents that react on the chip. The user may analyze these fluidic samples and/or their reaction products. More particularly, the user provides instructions to the computer 118 to activate the optical detection system 112 (step 292). The optical detection system 112 analyzes the reaction products (step 294), and provides the results of the analysis to the computer 118 which then displays the analysis results on the display 120 (step 296).

Figure 2:
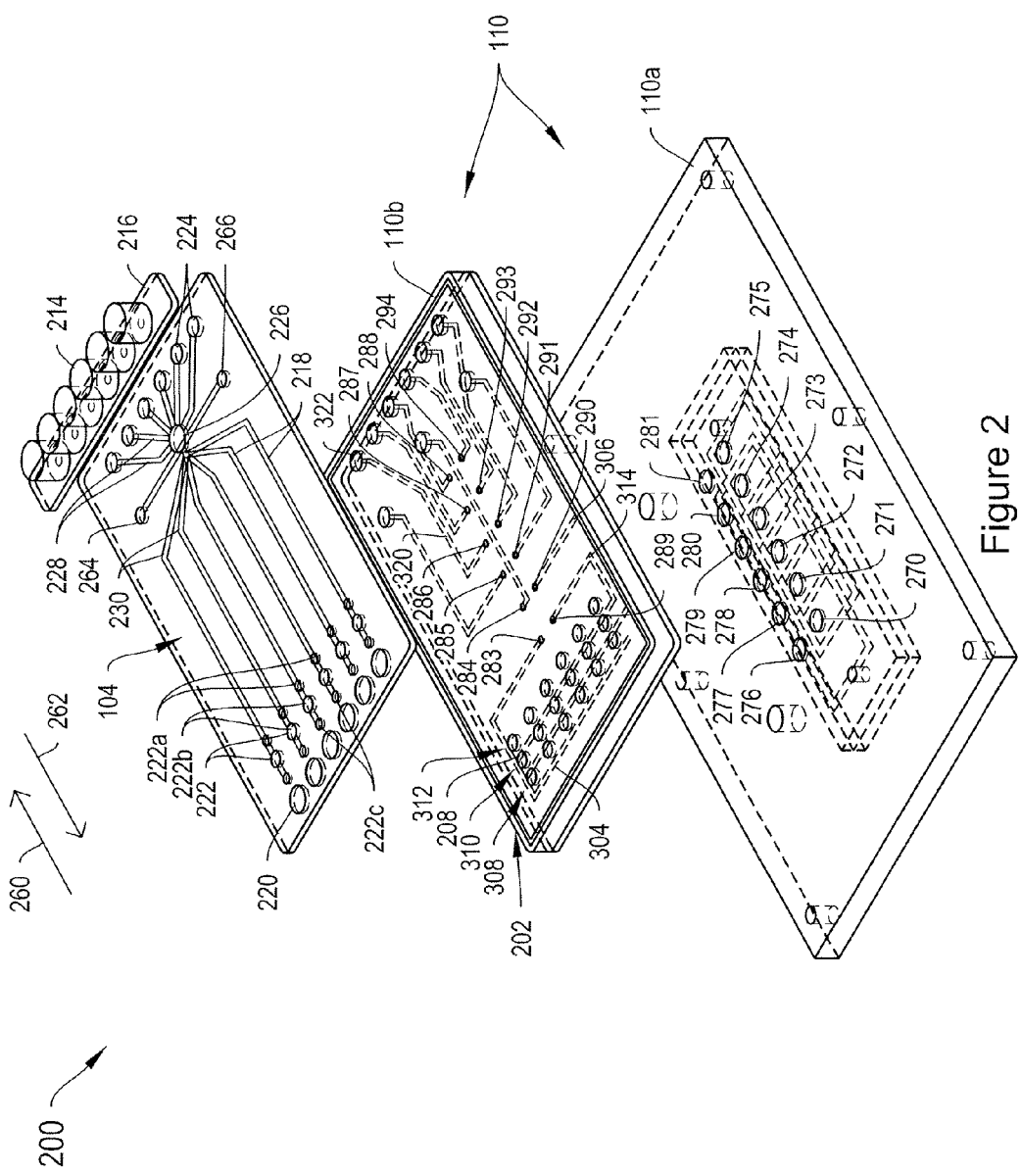
FIG. 2 shows a microfluidic chip assembly, according to an illustrative embodiment of the invention.

FIG. 2 shows a microfluidic chip assembly 200, according to an illustrative embodiment of the invention. The microfluidic chip assembly 200 includes the microfluidic chip 104 and the manifold structures 110 shown in FIG. 1, as well as a reagent cartridge 216 (not shown in FIG. 1) having a plurality of reagent reservoirs 214 that contain fluidic reagents.

As mentioned above, the microfluidic chip 104 includes a plurality of microfeatures, such as channels, valves, pumps, and/or reservoirs, for storing fluids, for routing fluids to and from various locations on the chip, and/or for reacting fluidic reagents. By way of example, the chip 104 includes a plurality of microfluidic channels 218, a plurality of channel pumps 222, a plurality of reagent valves 224, a dispensing valve 226, a first set of reagent channels 228, a second set of reagent channels 230, the reagent reservoirs 214, and the outlet reservoirs 220. The microfluidic channels 218, 228, and 230 can be of any suitable dimension, but in certain embodiments have cross-sectional diameters of between about 1 micron and about 500 microns, or between about 1 micron and about 50 microns. The microfluidic chip 104 generally includes a first substrate, and second substrate, and a membrane disposed therebetween. The above-described microfeatures are fabricated within one or more of the first substrate, the second substrate, and the membrane.

Figure 3B:
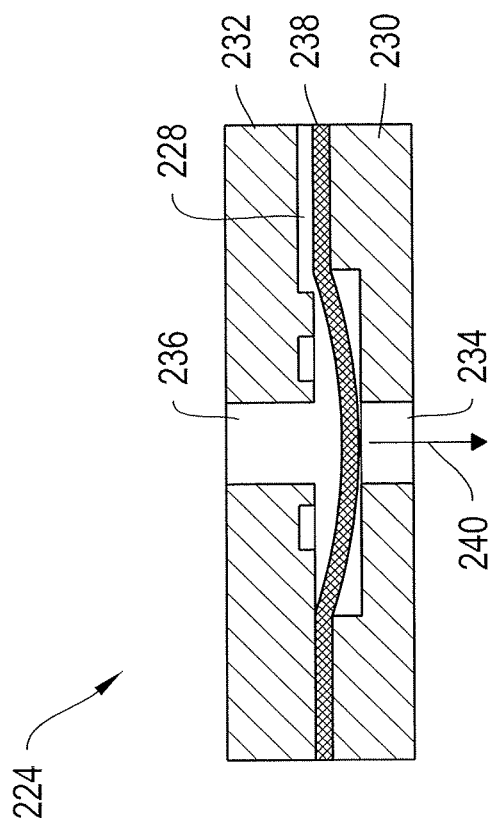
FIGS. 3A-B show a reagent valve having a first substrate, a second substrate, and a membrane, according to an illustrative embodiment of the invention.
Figure 3A:
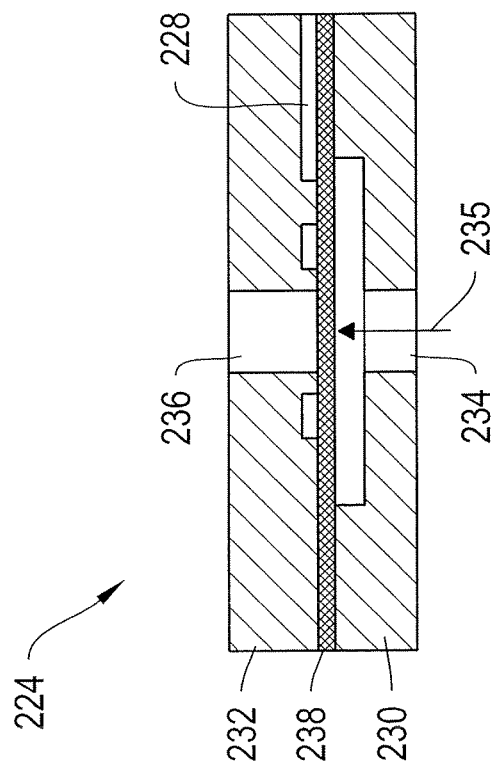

FIGS. 3A-B, by way of example, show a reagent valve 224 having a first substrate 230, a second substrate 232, and a membrane 238. The reagent valve 224 fluidly couples a reagent reservoir 214 to the channel 228. More particularly, each reagent reservoir 214 aligns with a respective valve 224. Fluid from the reagent reservoirs 214 flow into respective reservoir ports 236. In one exemplary implementation, fluid flows from a reagent reservoirs 214 in response to a user releasing a vacuum condition in the reservoir 214, which allows the fluid to freely fall from the reagent reservoir 214 into the reservoir port 236. When the valve 224 is actuated, the fluid in the reservoir port 236 flows to the channel 228.

As mentioned, the valve 224 includes a first substrate 230, a second substrate 232, and a membrane 238. The first substrate 230 has a drive chamber 234 fabricated therein. As depicted in FIG. 3A, a positive pneumatic force 235 through the drive chamber 234 closes the valve 224 by pressing the membrane upwards against the second substrate 232, thereby cutting off (or substantially cutting off) fluidic communication between the reservoir port 236 and the channel 228. In contrast, as depicted in FIG. 3B, a negative pneumatic force 240 through drive chamber 234 opens the valve by drawing the membrane 238 away from the second substrate 232, thereby fluidly coupling the reservoir port 236 to the channel 228. The depicted valve 224 is exemplary, and any valve structure known in the art can be used with this invention.

In order for the membrane 238 to draw towards or away from the second substrate 232, the membrane 238 is deformable. For example, the membrane 238 has a Young's modulus of between about 2 Gpa and about 4 Gpa and have a thickness, or width, selected for allowing deformation upon application of appropriate mechanical (e.g., pneumatic) force. The membrane 238 has a thickness of between about 10 μm and about 150 μm, or between about 15 μm and about 75 μm. The depicted first substrate 230 and the depicted second substrate 232 each has a thickness substantially larger than the thickness of the membrane 238, but in other implementations have thickness similar to or less than the thickness of the membrane 238.

In addition to fluidly coupling a reservoir port 236 to a channel 228, other valves can additionally or alternatively fluidly couple two or more channels to provide "one-to-many," "many-to-many," and/or mixing functionality. For example, referring again to FIG. 2, dispensing valve 226 fluidly couples the first set of reagent channels 228 to the second set of reagent channels 230. When only one of the first set of reagent channels 228 includes fluid (because, e.g., only that channel's respective valve 224 opens to port fluid from its respective reservoir 214 while all other valves 224 remain closed), the dispensing valve provides "one-to-many" reagent dispensing and processing. Namely, the contents of one reagent reservoir 214 flow to many outlet reservoirs 220. When a plurality of the first set of reagent channels 228 include fluid, the dispensing valve provides "many-to-many" reagent dispensing and processing. By selectively actuating certain ones of the reagent valves 224 and the dispensing valve 226, an operator can mix selected reagents from the reagent reservoirs 214 in the dispensing valve 226 region before the mixture is pumped to the outlet reservoirs 220.

FIGS. 4A-F show a channel pump 222, according to an illustrative embodiment of the invention. A microfluidic pump generally refers to any structure or group of structures capable of applying pressure to a fluid and/or facilitating the flow of fluid in one or more desired directions in a microfluidic device. The depicted pump 222 generally includes three valves: an inlet valve 222a, a drive valve 222b, and an outlet valve 222c, interconnected by portions 218b and 218c of the microfluidic channel 218. In operation, the pump 222 pumps fluid through the microfluidic channel 218 by cycling through six states that are activated sequentially to produce a peristaltic-like pumping effect.

Figure 4A:
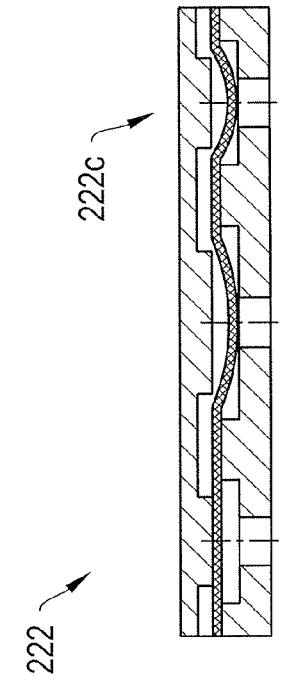
FIGS. 4A-F show a channel pump including three valves, according to an illustrative embodiment of the invention.
Figure 4B:
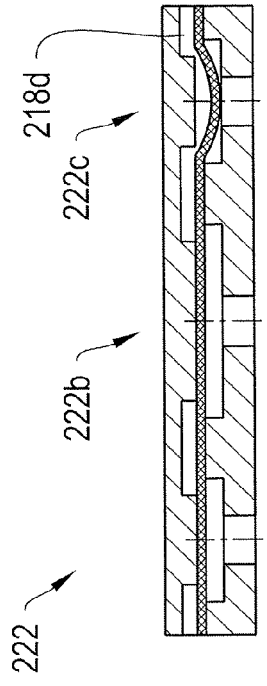
Figure 4C:
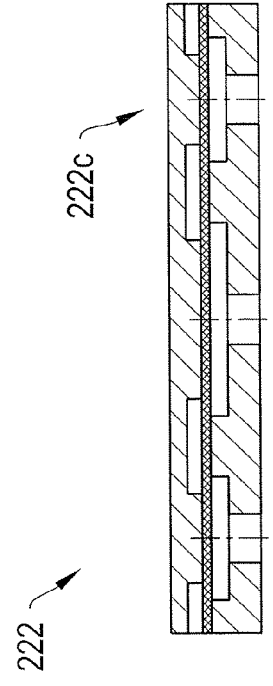
Figure 4D:
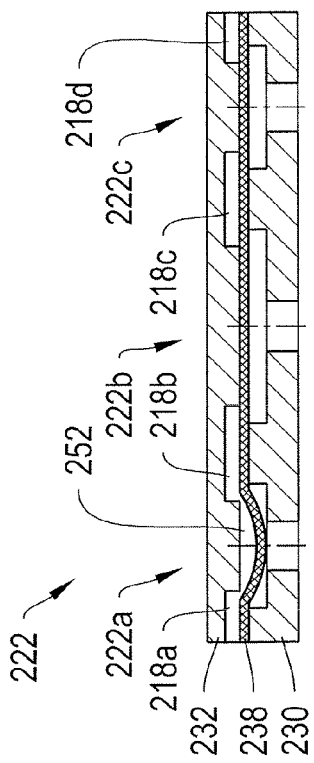
Figure 4E:
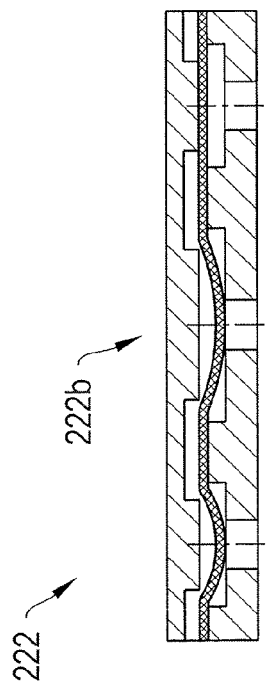
Figure 4F:
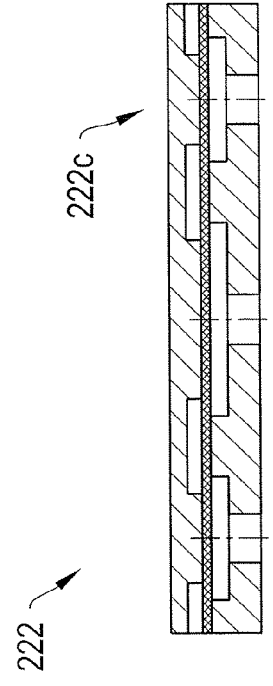

More particularly, in FIG. 4A, the inlet valve 222a opens and draws fluid from an inlet portion 218a of the microfluidic channel 218 into the volume 252 between the membrane 238 and the second substrate 232. In FIG. 4B, the drive valve 222b opens and draws more fluid into the pump system. In FIG. 4C, the inlet valve 222a closes. In FIG. 4D, the outlet valve 222c opens. In FIG. 4E, the drive valve 222b closes, and thereby forces fluid through the outlet valve 222c and into an outlet portion 218d of the microfluidic channel 218. In FIG. 4F, the outlet valve 222c then closes. These six states complete one pump cycle, displacing a volume of fluid through the pump.

The pump 222 is bidirectional. If the cycle is reversed, portion 218d is an inlet portion of the microfluidic channel 218, portion 218a is an outlet portion of the microfluidic channel 218, and fluid flows from portion 218d to portion 218a.

The valve structures 222a, 222b, and 222c are independently actuatable, in that any one of the valve structures can be actuated with little or substantially no effect on the state of the other valve structures. Those skilled in the art will recognize that alternate sequences of states may produce a pumping effect, and that other pumps can also be used with this invention.

Turning back to FIG. 2, we now describe exemplary fluid flow patterns on the chip 104. As mentioned above, the reagent cartridge 216 includes a plurality of reagent reservoirs 214 that hold fluidic reagents. The pumps and valves on the chip 104 generally transport fluid from the reagent reservoirs 214 to the outlet reservoirs 220 in accordance with a user-specified flow pattern.

More particularly, the chip 104 includes a plurality of reagent valves 224 that align with the reagent reservoirs 214. As mentioned above, the reagent valves 224 release fluid from respective reagent reservoirs 214 into respective microchannels 228 on the chip 104. A user may specify that one, certain ones, or all of the reagent valves will open. Next, the dispensing valve 226 opens to fluidly couple the first set of reagent channels 228 and the second set of reagent channels 230. The fluid from the first set of reagent channels 228 then flows to the second set of reagent channels 230. Next, the pumps 222 transport the fluid along the microfluidic channels 218. The user may specify that one, certain ones, or all of the pumps 222 transport the fluid.

In some cases, the fluids stored in the reagent reservoirs 214 will be reagents that chemically react with other reagents on the chip 104. For example, a user may specify that the reagent in a certain reservoir 214 will react with another reagent in another reservoir 214, in which case the corresponding reagent valves 224 and the dispensing valve 226 will actuate to mix the reagents, as was described above.

The reagents may also mix and react in the microfluidic channels 218. Moreover, additionally or alternatively, the microfluidic channels 218 themselves may include reagents. The reagents may be disposed in the microfluidic channels 218 in a number of forms. By way of example, the microfluidic channels 218 may include an insert strip (e.g., an insert membrane strip) with reagents coated or adhered thereto. In other implementations, the microfluidic channels 218 may include small spheres (i.e., spheroids or microspheres) coated with reagents.

For example, in one use the chip 104 performs a biological or chemical assay. In this use, the reagents in the microfluidic channels 218 are various biological and/or chemical samples. The reagent reservoirs 214 may include one or more of buffer wash, antibody, antibody with conjugated enzyme, and enzyme substrate. The contents of the reagent reservoirs 214 are released according to a user-specified sequence. The order and timing of release of the reagents from their respective reagent reservoirs 214 correspond to the steps of the particular assay method being used.

It may be desirable to allow these chemical reactions to incubate for longer periods of time within the microfluidic channels 218 by passing the fluids through the microfluidic channels 218 multiple times. As mentioned above, the channel pumps 222 can pump fluids bi-directionally, which allows back-and-forth fluid flow along the microfluidic channels 218. The bidirectional pumping repeatedly moves a reagent back 260 and forth 262 along the channels 218 to provide longer reaction time and greater reaction efficiency.

During these back-and-forth pumping cycles, air bubbles may form in the channels 218. The ventilation valves 264 and 266 vent the air bubbles to ambient air. Optionally, the outlet reservoirs 220 may also vent to ambient air to release the air bubbles.

Other fluid flow patterns are also possible. More particularly, by selectively operating the reagent valves 224, the distribution valve 226, and the channel pumps 222, fluid can flow in various combinations of flow patterns from the reagent reservoirs 214 to the outlet reservoirs 220. In particular, one or more specific reagents stored in the reagent reservoirs 214 may be selectively dispensed into assay channels at user-specified rates, in user-specified amounts, and at user-specified times, and then can be incubated in the channel and then stored and analyzed in the outlet reservoirs 220. Moreover, other microfluidic chip layouts with alternative configurations of valves, pumps, and reservoirs, may be used.

With continued reference to FIG. 2, the pneumatic forces described above that actuate the valves and pumps on the microfluidic chip 104 are provided by an array of solenoids that transmit pneumatic signals. The solenoids (not shown in FIG. 2, and to be described in more detail below) are located generally within and/or under the pneumatic manifold 110a, and attach to the pneumatic manifold 110a via attachment ports (not shown in FIG. 2) that will be described below. Each solenoid pneumatically couples to a respective aperture 270-281 and transmits pneumatic signals therethrough. In one exemplary implementation, each solenoid transmits a pneumatic signal that comprises positive pressure corresponding to the positive pneumatic force 235 of FIG. 3A, negative pressure (e.g., vacuum pressure) corresponding to the negative pneumatic force 240 of FIG. 3B, and/or sequences of positive and negative pressure.

The pneumatic signals are transmitted through the apertures 270-281 of the pneumatic manifold 110a to pneumatic ports 283-294 on the underside of the chip manifold 110b. The pneumatic ports 283-294 fluidly couple to pneumatic channels which route the pneumatic signals to appropriate pumps and valves on the chip 104. By way of example, aperture 276 transmits a pneumatic signal to pneumatic port 283. This pneumatic signal is transmitted through the pneumatic channel 304 to a plurality of valve ports 308. These valve ports 308 provide the positive or negative pneumatic force of the pneumatic signal to the valves 222c of the channel pumps 222. Similarly, the aperture 271 transmits a pneumatic signal to the pneumatic port 290, which fluidly couples to a channel 306. The channel 306 routes the pneumatic signal to the valve ports 310. The valve ports 310 provide the positive or negative pneumatic force, as the case may be, to the drive valves 222b of the channel pumps 222. Likewise, the aperture 270 transmits a pneumatic signal to the pneumatic port 289, which fluidly couples to a channel 314. The channel 314 routes the pneumatic signal to the valve ports 312. The valve ports 312 provide the positive or negative pneumatic force, as the case may be, to the valves 222a of the channel pumps 222.

As illustrated, the pneumatic signal from one solenoid (e.g., the solenoid coupled to aperture 270) may be routed to actuate several valve structures (e.g., the valves 222a). In the depicted exemplary implementation, by cycling the three solenoids that couple to apertures 270, 271, and 276 through positive pneumatic force and negative pneumatic force states appropriately, all of the channel pumps 222 operate simultaneously. However, in other implementations, certain channel pumps 222 may be independently actuatable by respective independent solenoids.

The above described aperture 270 actuates a plurality of valves 222a by routing a pneumatic signal along a single pneumatic channel 314. In other cases, an aperture may actuate a plurality of valves by routing the signal along multiple pneumatic channels. By way of example, several pneumatic channels may couple to a single pneumatic port, and route a pneumatic signal to several respective valve ports. Alternatively, a single pneumatic channel coupled to a single pneumatic port may branch into a plurality of channels that couple to respective valve ports.

Other solenoids actuate only one valve. For example, the solenoid coupled to aperture 279 transmits a pneumatic signal to the pneumatic port 286, which couples the signal to the channel 320 to route the signal to the valve port 322. As depicted, this pneumatic signal from aperture 279 actuates only one of the reagent valves 228.

Thus, as depicted, the chip manifold 110b includes channels that route pneumatic signals in accordance with a configuration of the valves in the microfluidic chip 104. Therefore, if a different application called for a replacement microfluidic chip with a different configuration of valves, then the user would only need to include a replacement for the chip manifold 110b that includes channels which route pneumatic signals in accordance with the configuration of valves on the replacement microfluidic chip. The user can continue using the other components of the microfluidic system 100, including the pneumatic manifold 110a, the controller 106, etc. This provides for an easily reconfigurable microfluidic system 100.

Figure 5:
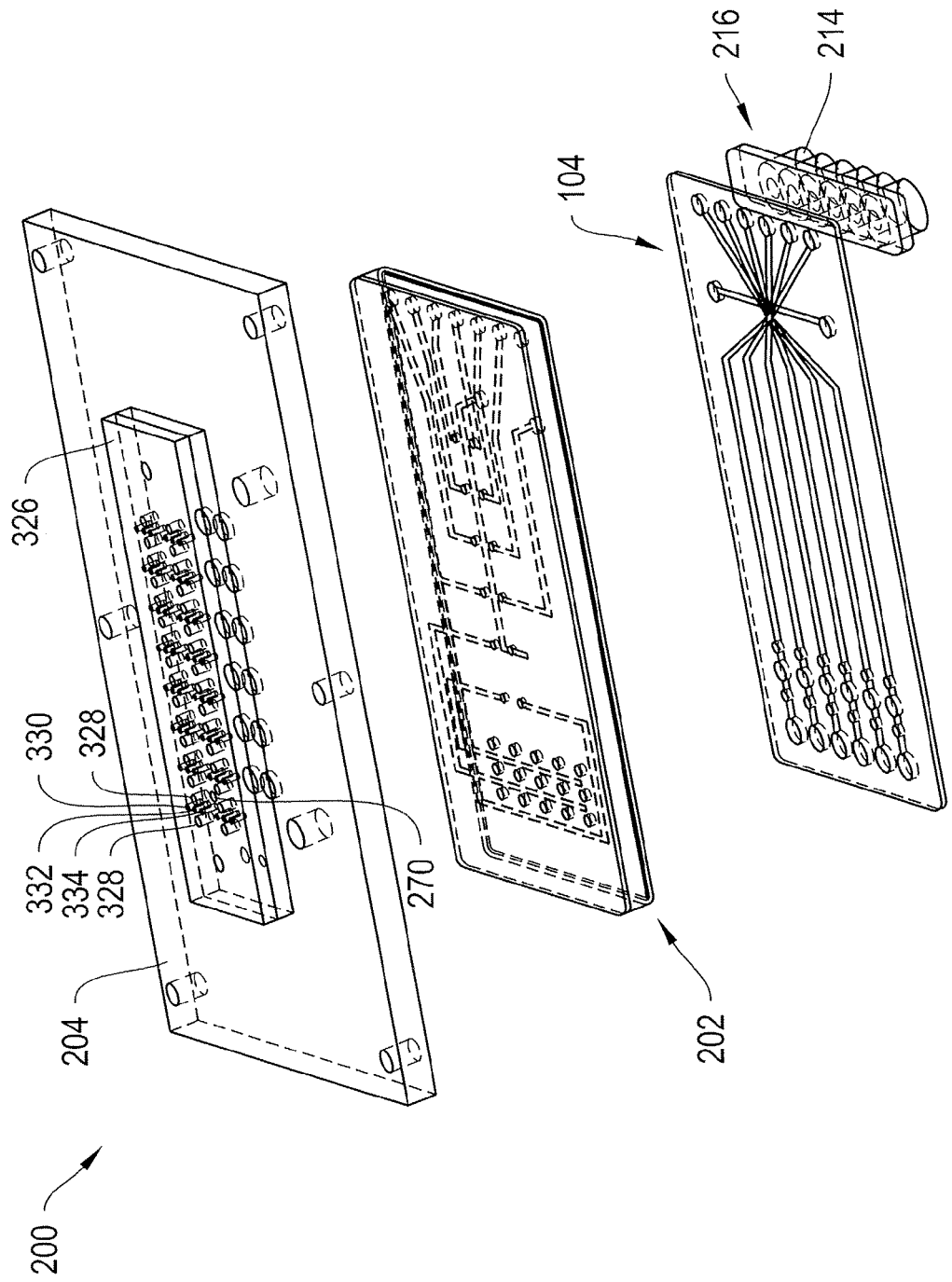
FIG. 5 shows a bottom view of the microfluidic chip assembly of FIG. 2.

FIG. 5 shows a bottom view of the microfluidic chip assembly 200. In addition to the chip 104, the reagent cartridge 216, and the chip manifold 202, FIG. 4 shows the pneumatic manifold 204 including a base 326 for mounting the solenoids to the pneumatic manifold 204, and for routing positive and negative pressure to and from the solenoids.

For each of the apertures 270-281 depicted in FIG. 2, the base 326 includes a plurality of corresponding ports. By way of example, for the depicted aperture 270, the base 326 includes: attachment ports which are depicted as the two mounting ports 328 (e.g., threaded screw slots) for attaching a solenoid (not shown) to the base 326, a pressure port 330 for providing a positive pressure to the solenoid, a vacuum port 332 for providing a negative (e.g., vacuum) pressure to the solenoid, and an output port 334 for switchable outputting one of the negative pressure and the positive pressure from the solenoid depending on an electrical signal transmitted to the solenoid from the controller 106.

Figure 6A:
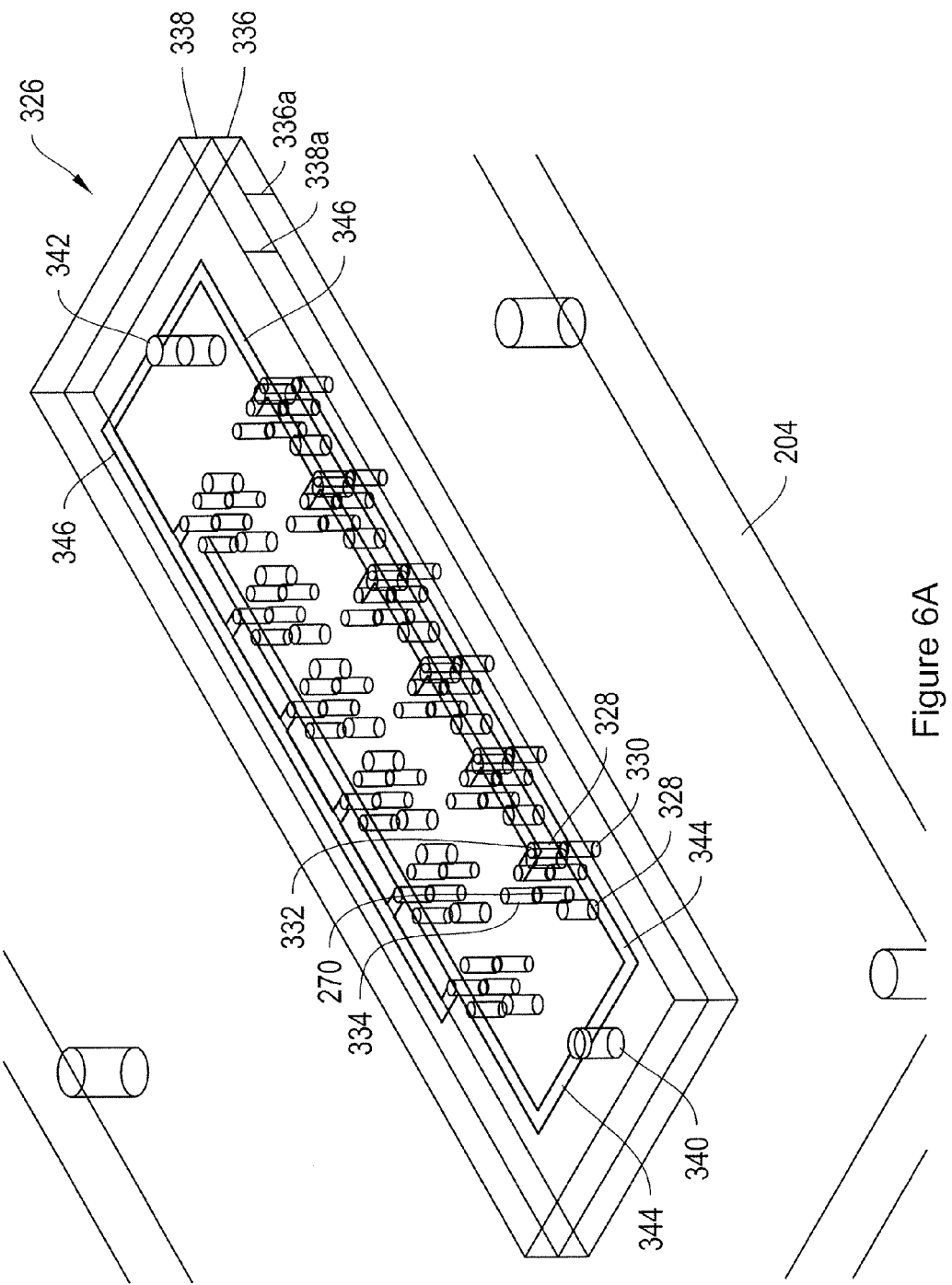
FIG. 6A shows a close-up of a top view of a pneumatic manifold including a base, according to an illustrative embodiment of the invention.
Figure 6B:
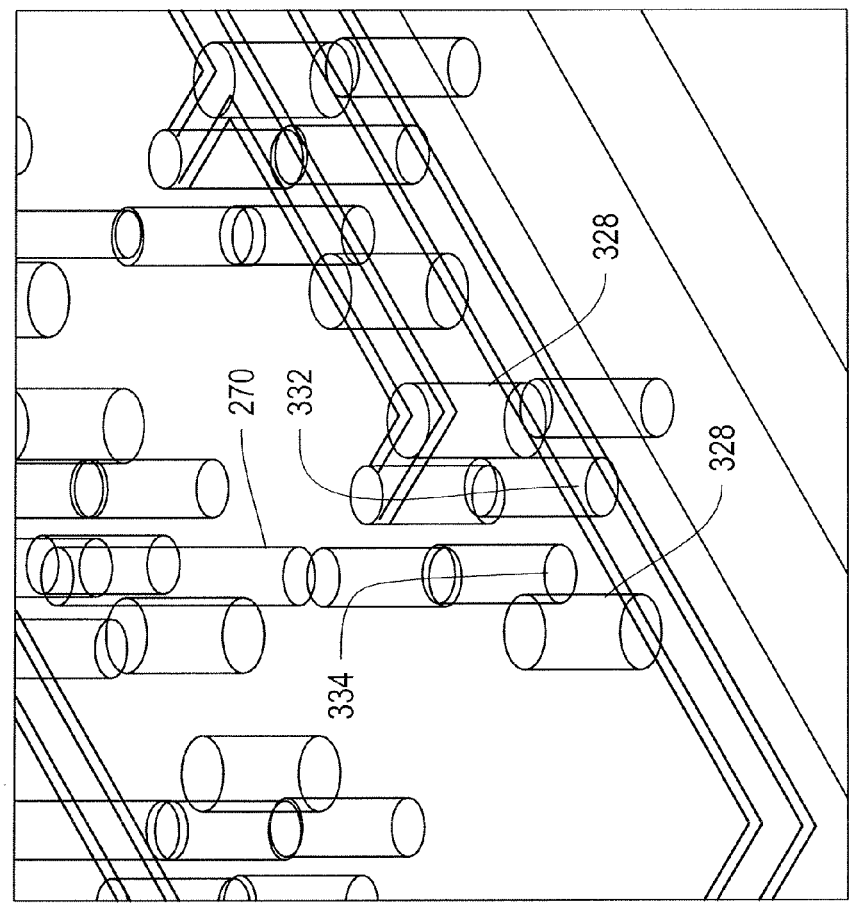
FIG. 6B shows a close-up view of the pneumatic manifold and base of FIG. 6A.

FIG. 6A shows a close-up of a top view of the pneumatic manifold 204 and the base 326, and FIG. 6B shows a close-up view of FIG. 6A. The base 326 includes two layers, a bottom layer 336 and a top layer 338. As mentioned above, the mounting ports 328 are used to attach a solenoid to the base 326. In one implementation, the mounting ports 328 are threaded screw slots, and the solenoid (not shown in FIGS. 6A-B) include screws that mate with the threaded screw slots. In the depicted embodiment, the mounting ports 328 span the width 336a of the bottom layer 336, but in other implementations may also extend through all or a portion of the top layer 338 and/or the through all layers of the pneumatic manifold 204.

As mentioned, the pressure port 330 provides a positive pressure to the solenoid and the vacuum port 332 provides a negative pressure to the solenoid. These pressures are provided, respectively, by a positive pressure source, depicted as the pressure inlet 340, and a negative pressure source, depicted as the vacuum inlet 342. In particular, a diaphragm pump 126, as depicted in FIG. 1, couples to the pressure inlet 340 and transmits a positive pressure therethrough. The pressure line 344 routes this pressure to the pressure port 330. Similarly, a diaphragm pump 126 couples to the vacuum inlet 342 and transmits a negative pressure therethrough. The vacuum line 346 routes this negative pressure to the vacuum port 332. In certain examples, diaphragm pumps 126 are small in size and are DC-powered so as to facilitate the portability of the microfluidic system 100. Accordingly, in certain embodiments, the systems may include a portable power supply, such as a battery or battery pack, that provides sufficient power to operate the DC powered diaphragm pump. The batteries may be rechargeable and in certain optional embodiments, the battery or battery pack may be incorporated into a power circuit that allows for battery operation or operation from wall current. Such power supply systems are known in the art and suitable power supply circuits may be employed without departing from the scope hereof.

In the depicted embodiment, the pressure inlet 340 extends through the width 336a of the bottom layer 336, while the vacuum inlet 342 extends through the width 336a and the width 338a of both the bottom layer 336 and the top layer 338, respectively. This may be beneficial so that the vacuum line 346 and the pressure line 344 can route pneumatic pressure (negative or positive, as the case may be) to the various pressure ports and vacuum ports of the base 326 without interfering with each other.

As mentioned above, the solenoid (not shown) switchably selects either the negative pressure provided by the vacuum line 346 or the positive pressure provided by the pressure line 344 depending on an electrical signal transmitted to the solenoid from the controller 106. The solenoid transmits the selected pressure through a solenoid output port 334. The depicted solenoid output port 334 extends through the bottom layer 336 and the top layer 338, and couples to the aperture 270 of the pneumatic manifold 204. As mentioned above, the aperture 270 then couples to the pneumatic port 289.

While the above-description was with respect to the exemplary aperture 270 and the associated ports 328, 330, 332, and 334 on the base 326, similar port structures switchably provide positive or negative pneumatic pressure from respective solenoids through respective apertures 270-276 to respective pneumatic ports 283-294.

Figure 7B:
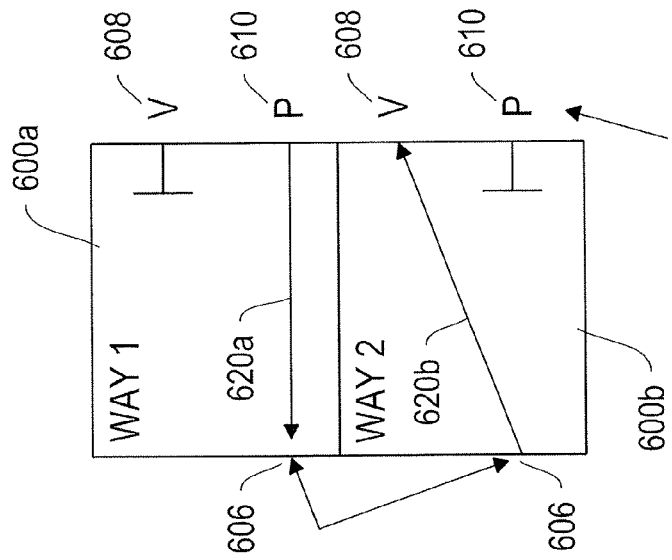
Figure 7B:
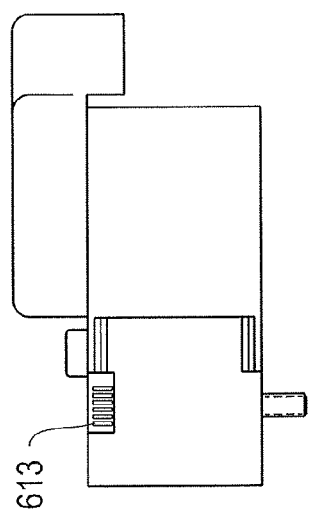
Figure 7C:
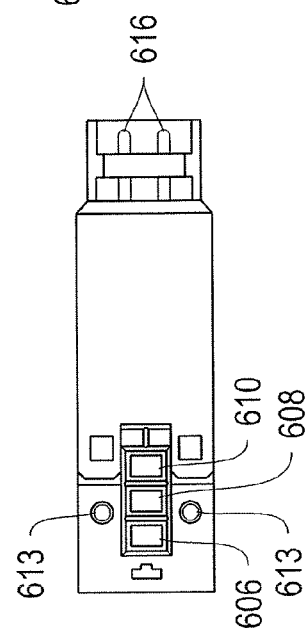
Figure 7A:
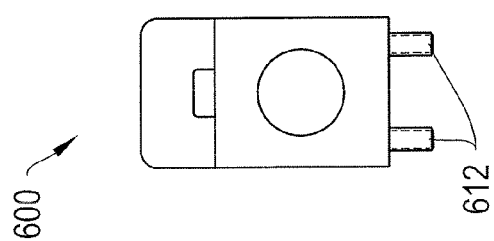

FIGS. 7A-D show a solenoid 600, according to an illustrative embodiment of the invention. More particularly, FIG. 7A shows a front view, FIG. 7B shows a side view, FIG. 7C shows a top view, and FIG. 7D shows a schematic representation of the solenoid 600. While the depicted embodiment uses solenoids such as solenoid 600, any other type of pneumatic transducer may be used.

As mentioned above, the solenoid 600 mounts to the base 326 via screw slots 328. The solenoid 600 includes mounting screws 612 which couple to the screw slots 328. The mounting screws include rotatable screw heads 613 that can be rotated by, e.g., a screw driver or a user's fingers.

Also as mentioned above, the solenoid 600 receives a positive pressure from the pressure inlet 340 via the pressure line 344, and a negative pressure from the vacuum inlet 342 via the vacuum line 346. The solenoid includes a pressure input 610 and a vacuum input 608 to receive these respective pressures.

Moreover, as mentioned above the solenoid 600 transmits either the positive pressure or the negative pressure, depending on an electrical signal transmitted to the solenoid 600 from the controller 106. Thus, the solenoid includes an electrical coupler 616 which in this embodiment is a standard two-pin plug. The controller electrically couples to the solenoid 600 via a cable having a socket for interfitting with the plug 616.

The solenoid 600 transmits the positive or negative pressure from either the vacuum input 608 or the pressure input 610, as the case may be, through the solenoid output 606 (e.g., an output port). FIG. 7D depicts the manner in which the solenoid 600 switches between the positive pressure and the negative pressure. In one embodiment, as illustrated by solenoid 600a of FIG. 7D, the pressure port 610 is connected to the output port 606 to transmit a positive pressure. In this case, air tends to flow from the pressure port 610 to the output port 606 as indicated by arrow 620a. In another embodiment, as illustrated by solenoid 600b, the vacuum port 608 is connected to the output port 606 to deliver a negative pressure flow. In this mode of pressure transmission, air tends to flow from the output port 606 to the vacuum port as indicated by arrow 620b. In certain embodiments, the output 606 transmits a positive pressure having a magnitude of less than about 50 psi, or between about 3 psi and about 25 psi, and a negative pressure having a magnitude of less than about 15 psi, or between about 3 psi and about 14 psi.

As described, the controller 106 transmits electronic signals that individually actuate respective solenoids (e.g., solenoid 600) in a sequence according to logic instructions. To do this, the controller 106 transmits electrical signals that actuate the solenoids (e.g., solenoid 600) to transmit either positive pressure or negative pressure. In one implementation, as discussed above, the controller 106 transmits the electrical signals in accordance with serial logic instructions from the computer 118. In another implementation, the controller 106 includes a memory that includes programmed logic instructions. In this case, the controller 106 need not be coupled to a computer 118.

In either case, the controller 106 translates the instructions to electronic signals that switch solenoids between positive pressure and negative pressure. In one implementation, the logic instructions comprise object-oriented source code including hierarchically related data structures, with each data structure corresponding to a particular type of instruction. The program logic instructions may reference data structures that comprise states of particular valves, data structures that comprise cycles of the states, and data structures that comprise sequences of the cycles.

For example, with continued reference to FIG. 2, the logic instructions may include instructions to shuttle fluid back and forth along a microfluidic channel 218. In order to do this, the logic instructions may define certain states for each of the valves 222a, 222b, and 222c of the channel pumps 222. One exemplary set of states includes two states of binary logic, namely '+' corresponding to an 'open valve' instruction, and '−' corresponding to a 'close valve' instruction. Thus, for the valves 222a-c, a list of states may include: {+222a, +222b, +222c, −222a, −222b, −222c}. The labeling of these states is exemplary, and the logic instructions may use other references for the states.

In other implementations, the chip 104 may include 3-way valves that switchably couple any two or more of three microfluidic channels. In this case, there may be five states of logic for the valve: one wherein no channels couple, one wherein all three of the channels couple, and three corresponding to the various combinations in which two of the three channels couple. This can be extended to valves that switchably couple any number of channels.

Returning to the exemplary channel pumps 222, a forward-pumping cycle may be defined based on the valve states as:

Pump Forward=[+222a, +222b, −222a, +222c, −222b, −222c]

which corresponds to the exemplary pumping cycle illustrated in FIG. 4. Similarly, a backward-pumping cycle may be defined as:

Pump Backward=[+222c, +222b, −222c, +222a, −222b, −222a].

A shuttle sequence may be defined based on these pumping cycles as:

Shuttle Fluid=[Pump Forward, Pump Backward, Pump Forward, Pump Backward, Pump Forward, Pump Backward, Pump Forward]

While the logic instructions may be implemented on the controller 106 using source code instructions such as those given above, the controller may additionally or alternatively use other implementations. By way of example, the controller may codify the logic instructions using one or more of programming languages based on C, C++, C#, COBOL, BASIC, Java®, assembly language, and like computer program languages.

As mentioned above, in some implementations the logic instructions are stored in a memory of the controller 106. They may be transferred into the memory from a computer (e.g., computer 118) using any suitable network connection, or programmed directly into the controller 106. Also as mentioned above, in other implementations the logic instructions are transmitted serially to the controller 106 from the computer 118.

Figure 8:
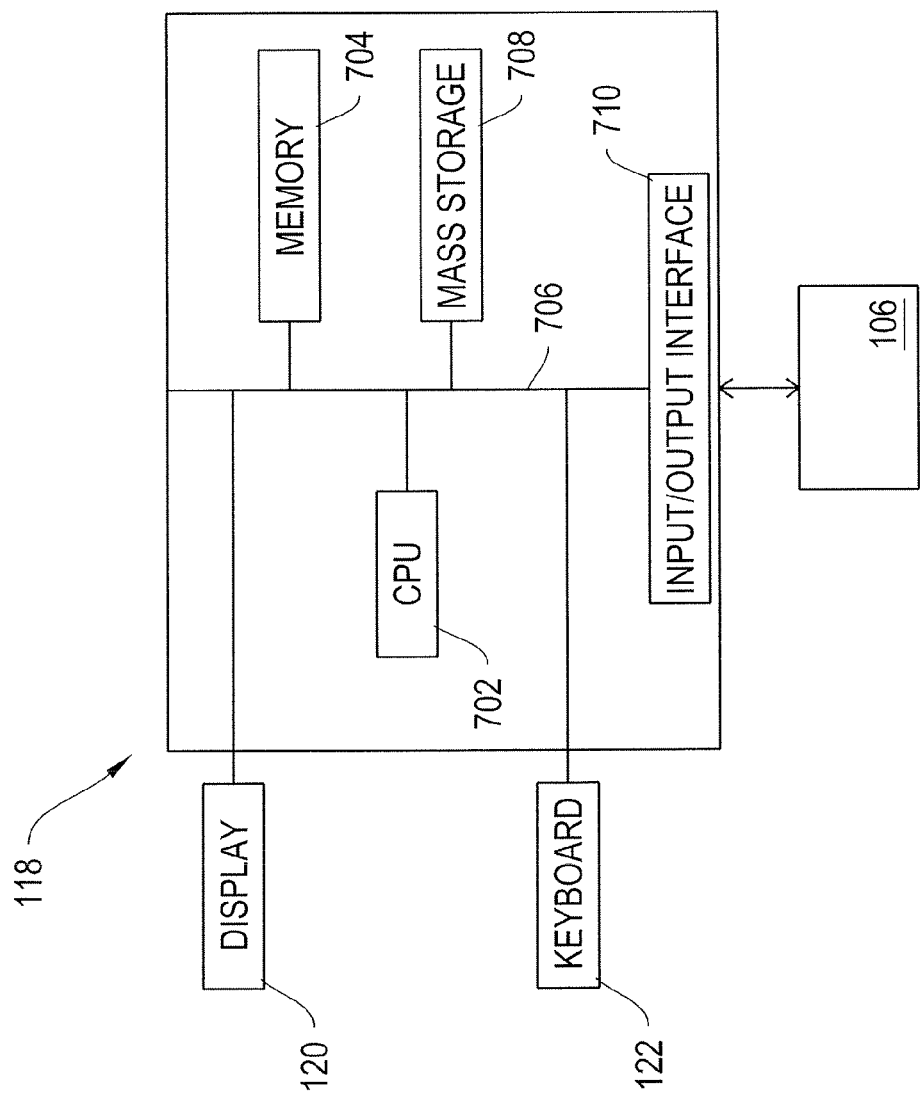
FIG. 8 shows an exemplary computer connected to the controller of FIG. 1, according to an illustrative embodiment of the invention.

FIG. 8 shows an exemplary computer 118 connected to the controller 106, according to an illustrative embodiment of the invention. The exemplary computer system 118 includes a central processing unit (CPU) 702, a memory 704, and an interconnect bus 706. The CPU 702 may include a single microprocessor or a plurality of microprocessors for configuring computer system 118 as a multi-processor system. The memory 704 illustratively includes a main memory and a read only memory. The computer 118 also includes the mass storage device 708 having, for example, various disk drives, tape drives, etc. The main memory 704 also includes dynamic random access memory (DRAM) and high-speed cache memory. In operation, the main memory 704 stores at least portions of instructions and data for execution by the CPU 702.

The mass storage 708 may include one or more magnetic disk or tape drives or optical disk drives, for storing data and instructions for use by the CPU 702. The mass storage system 708 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 118.

The computer system 118 may also include one or more input/output interfaces for communications, shown by way of example, as interface 710 for data communications to the controller 106. The data interface 710 may be a modem, an Ethernet card or any other suitable data communications device. The data interface 710 may provide a relatively high-speed link to a network, such as an intranet, internet, or the Internet, either directly or through an another external interface (not shown). The computer 118 may connect to the network, and communicate to the controller 106 when the controller 106 connects to the same network. The link may be, for example, optical, wired, or wireless (e.g., via satellite or cellular network). Alternatively, the computer system 118 may include a mainframe or other type of host computer system capable of Web-based communications via the network. The data interface 710 allows for delivering content, and accessing/receiving content via the network.

The computer 118 also couples to suitable input/output ports for interconnection with the display 120 and the keyboard 122 or the like serving as a local user interface for programming and/or data retrieval purposes. Alternatively, server operations personnel may interact with the computer 118 for controlling and/or programming the system from remote terminal devices via a network, such as the exemplary networks discussed above.

The computer system 118 may run a variety of application programs and stores associated data in a database of mass storage system 708.

The components contained in the computer system 118 are those typically found in general purpose computer systems used as servers, workstations, personal computers, network terminals, and the like. In fact, these components are intended to represent a broad category of such computer components that are well known in the art.

While the above description was given in connection with the computer 118, it may also apply to the controller 106. More particularly, the controller 106 may include all or some of the components of the computer 118 described in connection with FIG. 8.

As mentioned above, in certain implementations the fluids are reagents that react on the chip, and the user then analyzes the reaction products. By way of example, the reagents may react in the microfluidic channels 218 using the bi-directional pumping of the channel pumps 222, after which the channel pumps 222 transport the fluid into the outlet reservoirs 220. The optical detection system 112 analyzes the reaction products as they flow to the outlet reservoirs 220.

Figure 9:
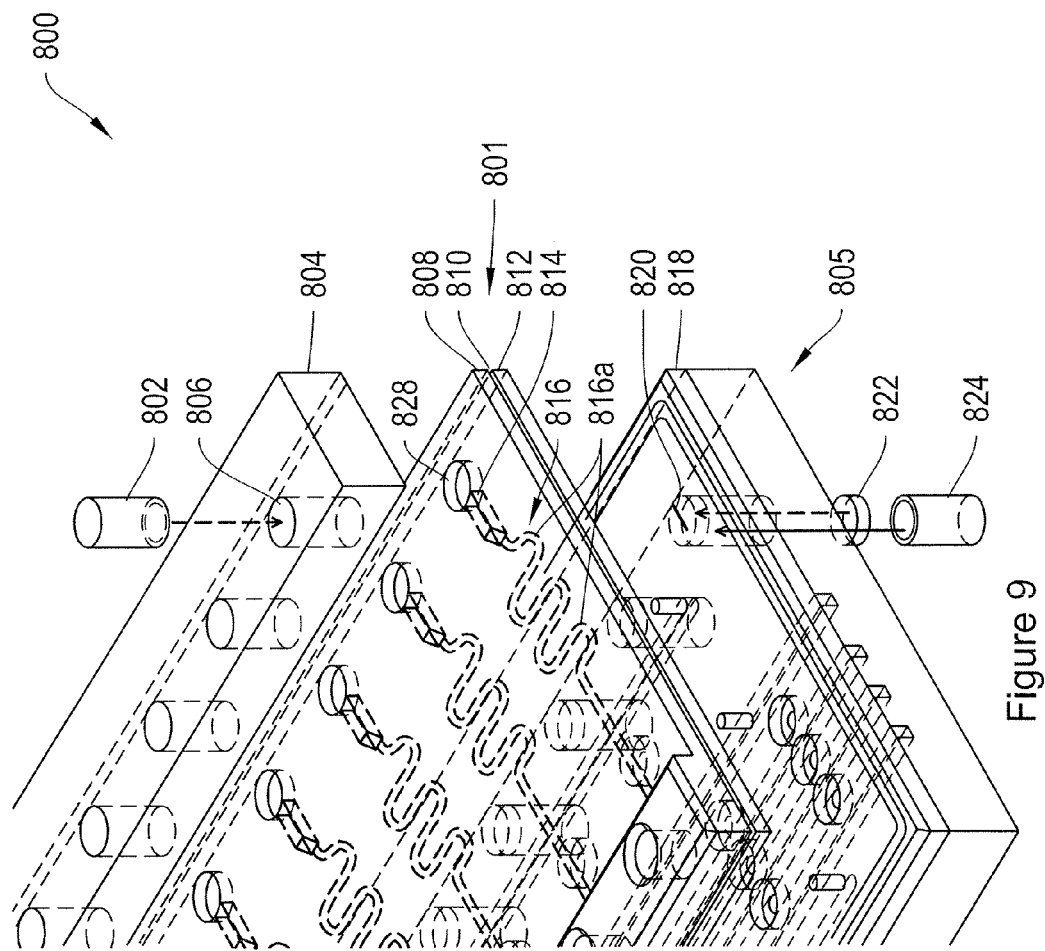
FIG. 9 shows an exemplary detection system, according to an illustrative embodiment of the invention.

FIG. 9 shows an exploded view of an exemplary detection system 800 similar to the optical detection system 112 of FIG. 1, according to an illustrative embodiment of the invention. More particularly, the system 800 includes a microfluidic chip 801, similar to the microfluidic chip 104 of FIG. 1, a light housing 804, and a detector assembly 805. The depicted detection system 800 analyzes reaction products by detecting analyte concentrations of the reaction products.

The microfluidic chip 801 includes a plurality of microfluidic channels 816 that transport fluid to outlet reservoirs 828. The microfluidic channels 816 are similar to the microfluidic channels 218, but have winding portions 816a having a plurality of curves. The plurality of curves increase the distance that reagents must flow along the microfluidic channels 816 when compared to linear channels (e.g., microfluidic channels 218). This may be beneficial when fluidic reagents are reacting in the channel 816, since the reagents take a longer amount of time to travel the increased distance, and this increases the reaction incubation time.

Before entering the outlet reservoir 828, the fluid flows through a detecting window 814 where it is characterized by the detection system 800. Generally, the detection system 800 in the depicted implementation characterizes the fluid in the detection window 814 by measuring its interaction with light. The light housing 804 includes light sources 802 that transmit light through the detecting window 814. The detector assembly 805 includes photodiodes 824 that receive the light after it is transmitted through the detecting window 814, and output signals related to the amount of light they receive. These signals are mapped into analyte concentration measurements.

More particularly, if a detecting window includes a fluid with a high analyte concentration, more of the light will be absorbed by the analyte and the output signal of the photodiode 824 will be lower. Thus, based on the output signal of the photodiode 824, the system 800 quantifies the absorbance of the sample, and either directly uses the absorbance as a measure of the analyte concentration, or maps the absorbance into an actual analyte concentration (e.g., a relative concentration).

More particularly, the absorbance value A of sample at a specific wavelength of light can be given by Beer's Law:

$$A = \epsilon l c \quad (1)$$

where c represents the concentration c of the analyte's molecule, l represents the optical path length (i.e., the distance of the detecting window 814 through which the light travels), and $\epsilon$ is a constant of proportionality referred to as absorptivity or molar extinction coefficient if the concentration is measured in moles/liter.

The absorbance value A of a sample can be measured from the output signal of the photodiode 824 as:

$$A = -\log\left(\frac{I_s - I_d}{I_r - I_d}\right) \quad (2)$$

where $I_s$ represents the output signal of the photodiode 824 in response to the sample being measured, $I_d$ represents the output signal of the photodiode 824 under dark conditions, and $I_r$ represents the output signal of the photodiode 824 in response to a reference fluid. The absorbance A can then, optionally, be mapped to a concentration c using Beer's Law (Equation (1)).

More particularly, the light housing 814 includes a plurality of apertures 806, in which the light sources 802 are disposed. The light sources 802 align with respective detecting windows 814 and transmit light therethrough. In one implementation, the light source is an LED with a spectral half width of less than about 60 nm. However, other types of light sources may be used. In particular, the light sources may transmit light of various wavelengths (e.g., the light need not be visible), with various intensities, and with various polarization characteristics. In one use, the light has at least sufficient intensity such that at least some of the light transmits entirely through the detection window 814 in detectable amounts.

In certain embodiments, each of the light sources 802 is adjustable. The light sources 802 may be collectively adjustable, so that a technician can optimize the performance of the system 800. The light sources 802 may, additionally or alternatively, be individually adjustable, so that a technician can further adjust individual ones of the light sources 802 to further optimize the performance of the system 800. Exemplary adjustable parameters includes intensity, wavelength, bandwidth, and polarization.

As mentioned, the light sources 802 transmit light through the detecting window 814. The light is then detected by the detector assembly 805. In particular, the detector assembly 805 includes a photo-mask 818 having a plurality of viewing slits 820. The photo-mask attenuates (or eliminates) ambient light so that the ambient light does not interfere with detections of the light transmitted by the light source 802. More particularly, the viewing slit 820 is depicted as a narrow and elongate slot, and attenuates stray, broad spectrum light. As a result, when the detector is placed in an uncontrolled environment, such as a lighted room or an outdoor environment with variable ambient lighting, the output signal of the photodiode $I_s$ is not distorted by the varying ambient light. In other embodiments, instead of a slit 820, the photo-mask 818 may include other configurations of apertures.

The detector assembly 805 also includes band-pass filters 822. The band-pass filters 822 also serve, in part, to filter out ambient light. Thus, in certain implementations, the band-pass filters 822 are tuned to substantially similar wavelength ranges as the light sources 802.

The band-pass filters 822 also serve to maintain a linear relationship between the concentration of the analyte and the absorbance A as it is calculated based on the output signal of the photodiode 824. This linear relationship may be beneficial for a variety of reasons, including analytical simplicity and reproducibility and standardization of analytical results.

More particularly, as indicated above with respect to Equation (1), the absorbance of a sample is linearly related to the concentration of that sample for a particular wavelength. However, as mentioned above, the light sources 802 may transmit light having a bandwidth substantially wider than just a single wavelength. Thus, the linear relationship of Equation (1) may not hold. Therefore, in certain embodiments, the band-pass filters 822 are monochromators that pass-through only a single wavelength (e.g., a technician-selected wavelength) of the light from the light sources 802. However, in certain cases a monochromator may be prohibitively large and/or expensive. Thus, the band-pass filters 822 may comprise smaller and/or more inexpensive filters having wider pass bands that provide a sufficiently linear relationship between a sample's absorbance and its analyte concentration. The passband may be less than about 20 nm, less than about 10 nm, or less than about 5 nm.

Light that travels through the band-pass filters 822 is detected by the photodiodes 824. The photodiodes may comprise any photodiode variation known in the art. In one aspect, the photodiodes include built-in trans-impedance amplifiers which provide increased detection sensitivity.

The increased detection sensitivity may be desired because, in certain exemplary uses, varying analyte concentrations in the fluid samples result in only small variations in light intensities at the photodiodes 824. In order to amplify these small variations, the photodiode may use feedback resistors with high resistances (e.g., more than about 300 Mohm or more than about 400 Mohm). In some implementations, the photodiode may includes a discrete component operational amplifier in combination with the feedback resistors, but this may result in slow responses, signal distortion, and channel-to-channel variability. Therefore, in other implementations, the photodiode comprises a CMOS integrated photodiode in combination with a trans-impedance amplifier, which can provide high detection sensitivity and low fabrication costs. Although the above-description is with respect to the photodiodes 824, any suitable transducer may be used in their place.

Figure 10:
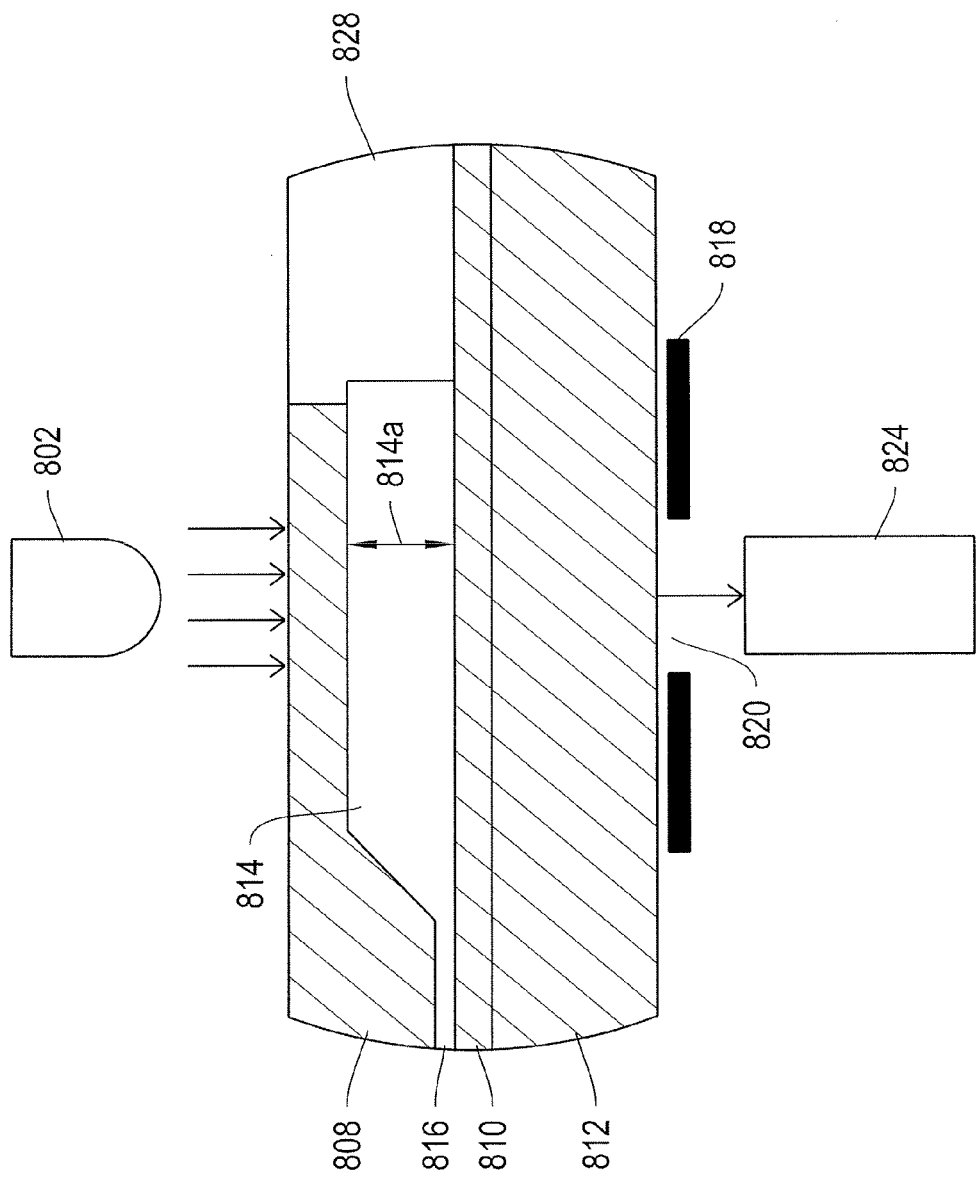
FIG. 10 shows a close-up side view of a detecting window and associated detection components, according to an illustrative embodiment of the invention.

FIG. 10 shows a close-up side view of a detecting window 814, according to an illustrative embodiment of the invention. As shown, the microfluidic chip 801 includes a top substrate 808, a bottom substrate 812, and a membrane 810 disposed therebetween. The detecting window 814 is formed within the top substrate 808 of the microfluidic chip 801. The detecting window 814 couples to a microfluidic channel 816, which transfers fluid to the detecting window 814, and to a waste/outlet reservoir 828, which receives the fluid after it is detected.

As shown, the detecting window 814 has larger dimensions (e.g., cross-sectional height and width) than the channel 816. This may be beneficial for several reasons. A detecting window 814 that is too small may result in undetectable signals from the photodiode 824. A larger detecting window 814 allows more of the sample in the detecting window 814, and can result in more detection sensitivity.

Additionally, a larger detecting window 814 results in a greater optical path length 814a, which also improves the detection sensitivity. More particularly, as mentioned above with respect to Beer's Law (Equation (1)), the absorbance A of a sample is linearly related to the optical path length 814a, denoted as l in Equation (1). Therefore, a larger optical path length 814a results in larger magnitudes of change in the absorbance A for a given change in concentration c. The larger magnitudes of change are easier for the photodiode 824 to detect, and thereby result in increased detection sensitivity.

While a larger detecting window 814 has benefits, in certain implementations the volume of the detecting window 814 is kept within certain limits. If the volume of the fluid in the detecting window 814 deviates significantly from the volume of the fluid processed in the channel 816, the detector's performance may degrade. By way of example, a very large detecting window 814 may prolong the concentration balance time (i.e., the time required for the concentration of the analyte to substantially homogenize throughout the sample).

While various dimensions may be suitable in view of the above considerations, in certain embodiments the channel 816 has a cross-sectional height of between about 1 micron and about 50 microns, or between about 3 microns and about 20 microns, while the detecting window 814 has a cross-sectional height 814a of between about 50 microns and about 750 microns.

In addition to its size, the orientation of the detecting window 814 improves the detection sensitivity of the system 800. In the depicted configuration, the light source 802 and the photodiode 824 are oriented along an axis perpendicular to the main plane of the chip 801 and the detecting window 814. This perpendicular orientation may be beneficial so a technician does not need to realign the photodiodes 824, detecting windows 814, and light sources 802. More particularly, in one implementation the distance between the light sources 802 and the photodiodes 824 is adjustable by, e.g., adjusting the vertical distance between the light sources 802 or the photodiodes 824 and the chip 801. As a result of the perpendicular orientation, a technician can easily vertically adjust the light sources 802 and/or the photodiodes 824 to optimal locations without having to realign them with the detecting window 814.

Figure 11:
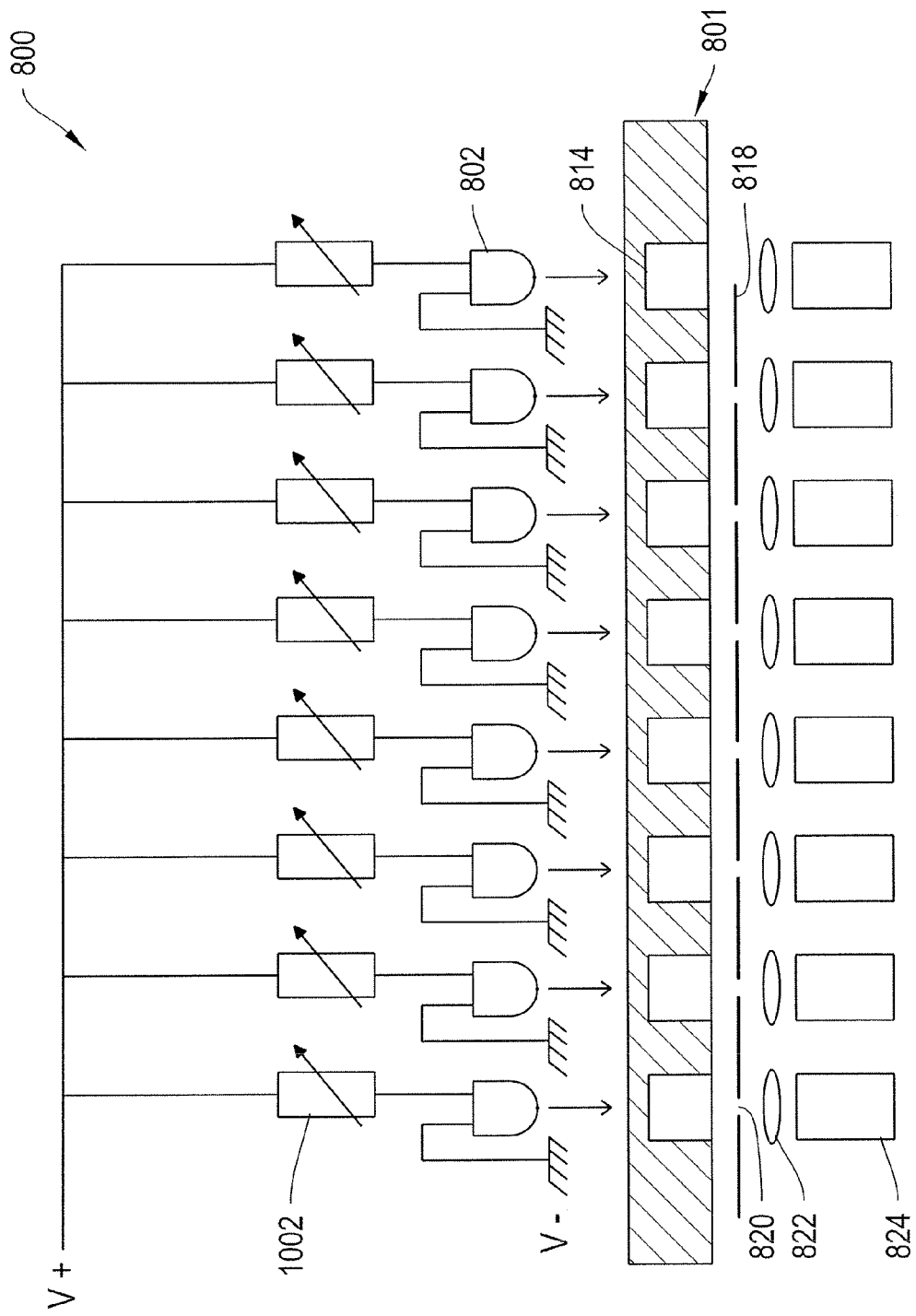
FIG. 11 shows a more detailed front view of the detection system of FIG. 9.

FIG. 11 shows a more detailed front view of the detection system 800. As depicted in previous figures, FIG. 11 shows the light sources 802, the detecting windows 814, the photo-mask 818 with slits 820 disposed therein, the band-pass filters 822, and the photodiodes 824.

Also shown is a voltage source labeled as V+, and electrical ground labeled as V−, both of which couple to the light sources 802 in order to provide a voltage differential that powers the light sources 802. The voltage differential may come from any suitable source, such as an electrical wall outlet, a battery, or a fuel cell (e.g., a micro-fuel cell). Each of the light sources couples to the voltage source V+ through a series connection with a current-limiting adjustable resistor 1002. The adjustable resistors 1002 can be individually adjusted to alter the amount of current driving the respective light sources 802 and thereby alter the intensity of the light source 802. In use, a technician calibrates the resistance of each of the resistors 1002 in order to compensate for manufacturing variations and other sources of variation in the light sources 802, the band-pass filters 822, the photodiodes 824, the detecting windows 814, or any of the other components described herein.

More particularly, in one use the technician fills each of the detecting windows 814 with a common reference buffer. The technician then powers the light sources 802 and monitors the output signals from the photodiodes 824. These reference output signals were described above in connection with Equation (2) and referred to as $I_r$. The manufacturer adjusts each of the adjustable resistors 1002 so that the corresponding output signal $I_r$ is substantially as high as can be achieved without saturating the corresponding photodiode 824. Since $I_d$ is a characteristic constant of the photodiode under "dark" conditions and its value is often significantly smaller than $I_r$ for a given system noise level, maximizing $I_r$ can improve the signal/noise ratio of the output signal of the photodiode 824 and increase the dynamic range of the detections. However, other methods for calibrating the resistors 1002 may also be used. For example, a digital to analog converter is used with a computer control to automate the calibration process.

FIG. 12 shows a close-up front view of the detection components associated with one exemplary detecting window 814, according to an illustrative embodiment of the invention. As shown, a chamber 825 tightly fits therein the photodiode 824 and the band-pass filter 822. The band-pass filter 822 is substantially coplanar with the surface 805a of the detector assembly 805 and is substantially perpendicular to the viewing slit 820. The viewing slit 820 has a smaller lateral dimension than the detecting window 814, so that the entire open area of the viewing slit 820 is completely covered by the detecting window 814 (as will be shown more clearly in a subsequent figure). This ensures that the light that passes through the sample in the detecting window 814 is measured by the photodiode 824, while ambient light is attenuated. The light that passes through the detecting window 814, the viewing slit 820, and the band-pass filter 822 is then received by the photodiode 824. In the depicted embodiment, the photodiode 824 includes a sensing element 827 which detects the light.

FIG. 13 shows a top view of the detection components associated with one exemplary detecting window 814. As shown, the detecting window 814 completely covers the viewing slit 820. Also shown is the band-pass filter 822 and the sensing element 827.

Exemplary experimental results are now described in connection with FIGS. 14-18. In the experiment, eight fluid samples were transported on a microfluidic chip (similar to chips 104 and 801) through eight respective microfluidic channels and into corresponding detecting windows. The detection components used for the detecting windows included LEDs having peak emissions of 430 nm, bandpass filters having a center frequency of 430 nm and a bandwidth of 10 nm, and photodiodes having internal trans-impedance amplifiers. The electrical output signals from the photodiodes were transmitted onto a National Instruments signal board and processed by a customized Labview application. The eight samples had the following eight relative concentrations: 0.0, 0.2, 0.4, 0.6, 0.8, 1.0, 1.2, and 1.4.

Figure 14:
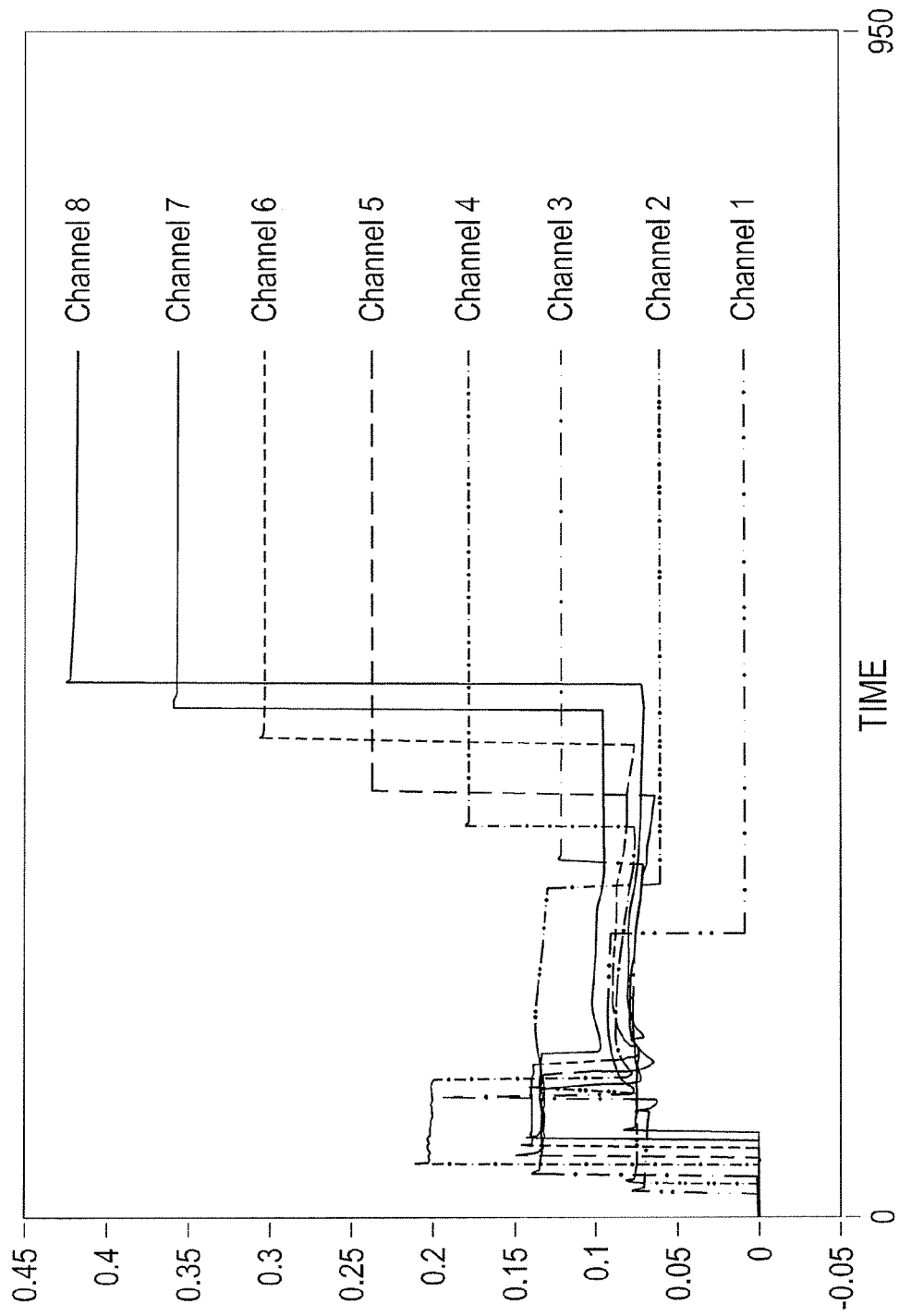
FIG. 14 shows absorbance measurements of samples taken from an electronic signal board, according to this experimental use of the invention.

FIG. 14 shows the absorbance measurements taken from the National Instruments board according to this experimental use of the invention. Each of the eight depicted waveforms corresponds to the output signal of one of the eight photodiodes. Each of the waveforms settles near a value that corresponds to the measured absorbance of the corresponding fluid sample.

Figure 15:
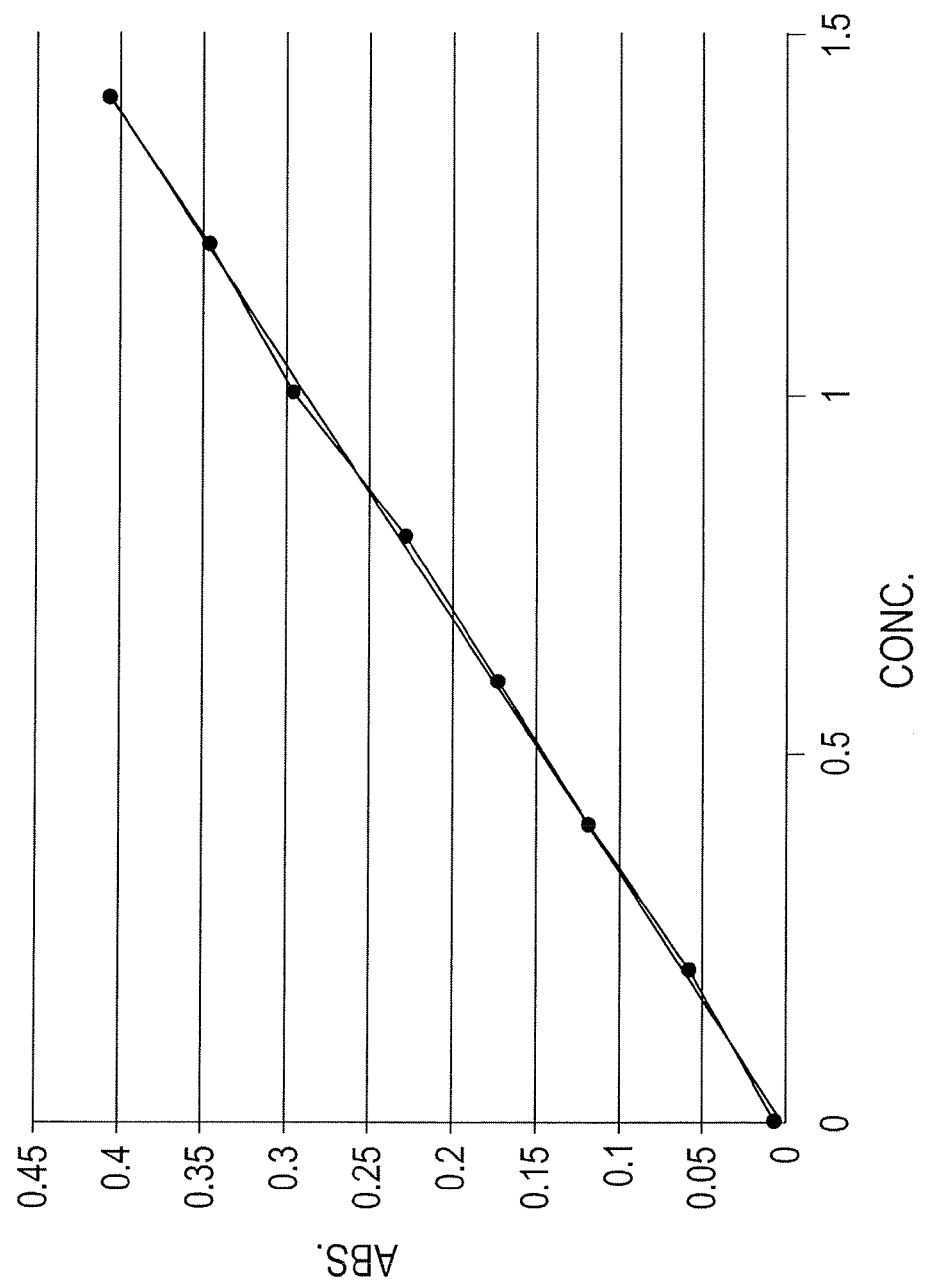
FIG. 15 shows a line plot of the absorbances of the samples of FIG. 14, set forth on a vertical axis, as a function of the concentration of the samples, set forth on a horizontal axis.

FIG. 15 shows a line plot of these absorbances, set forth on the vertical axis, as a function of the concentration of the samples, set forth on the horizontal axis. Also shown is a line of best fit, derived through a linear regression. As shown, the absorbance satisfies a near-linear relationship with the concentration, as desired. The coordinates of the plotted points are set forth below in Table 1.

TABLE 1

| | Channel | | | | | | | |
|---|---|---|---|---|---|---|---|---|
| | 1 | 2 | 3 | 4 | 5 | 6 | 7 | 8 |
| Conc. | 0 | 0.2 | 0.4 | 0.6 | 0.8 | 1.0 | 1.2 | 1.4 |
| Abs. | 0.009 | 0.060 | 0.121 | 0.177 | 0.235 | 0.302 | 0.355 | 0.417 |

In one aspect, the detection system 800 described above, which includes separate detection components for each detecting window 814, is an inexpensive and portable alternative to commercially available spectrometers. However, the detection system 800 results in little or no performance loss.

Figure 16:
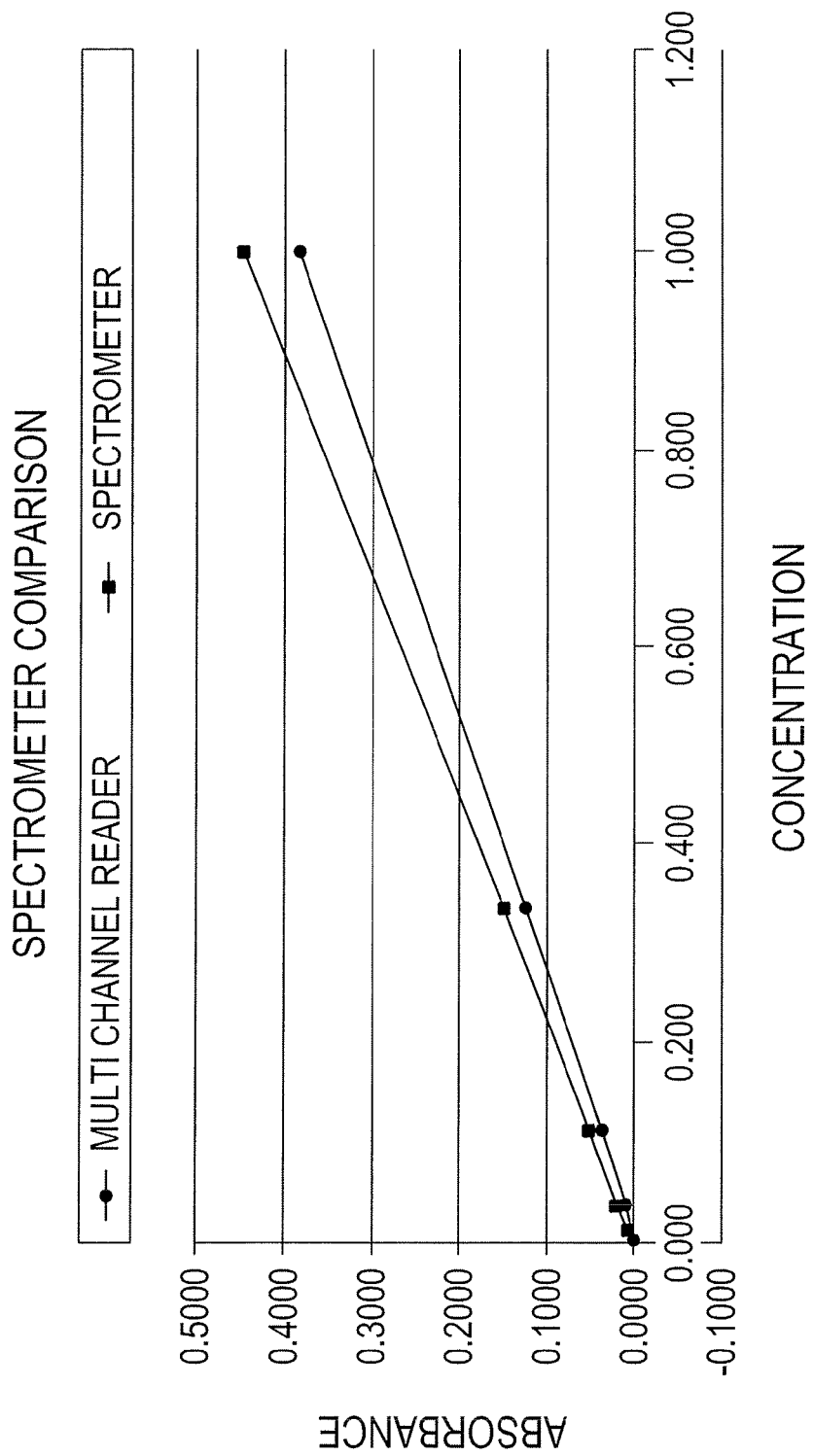
FIG. 16 shows sample plots of absorbance as a function of concentration according to an experimental use of the invention.

FIG. 16, by way of comparison, shows sample plots of absorbance as a function of concentration. The plot labeled with squares is for a commercially available spectrometer, and the plot labeled with triangles is for the detection system 800 described herein. As shown, the plots are substantially similar, and in particular both plots very closely align with their linear best fits, which are plotted but not visible since they align so closely with their corresponding plots.

Figure 17:
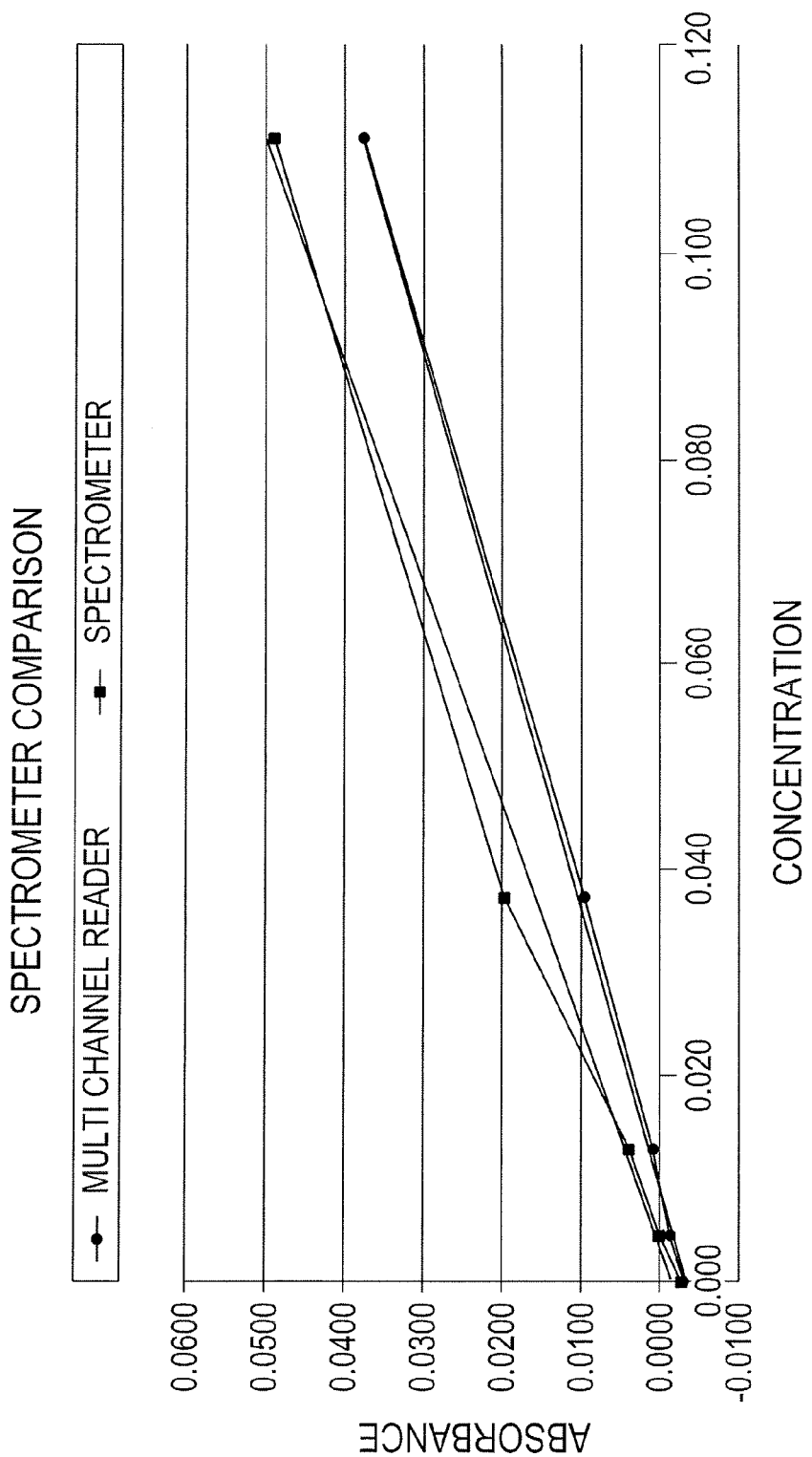
FIG. 17 shows sample plots according to an experimental use of the invention wherein the fluidic samples have lower concentrations that those used for FIG. 16.

FIG. 17 shows sample plots wherein the fluidic samples have lower concentrations. Again the plot labeled with squares corresponds to the commercially available spectrometer, while the plot labeled with diamonds corresponds to the detection system 800 described herein. As show, at these lower concentrations the detection system 800 produces a plot that more closely aligns with its line of best fit than does the commercially available spectrometer. Thus, at lower concentrations the detection system 800 may offer superior performance.

As mentioned above, the microfluidic chip 104 described above generally includes a top substrate 232, a bottom substrate 230, and a membrane 238 disposed therebetween. The microfeatures (e.g., pumps, valves, or reservoirs) are fabricated in one or more of the top substrate 232, the bottom substrate 230, and the membrane 238. In certain embodiments, the top substrate 232, the bottom substrate 230, and the membrane 238 are all made of plastic. Exemplary materials include non-elastomeric polymers, such as polymethyl methacrylate, polystyrene, polycarbonate, and acrylic. These materials are beneficial at least in part because they are reasonably rigid, which is suitable for the top substrate 232 and the bottom substrate 230. Moreover, these materials can be deformable when used in thin layers, which is suitable for the membrane 238 which, as mentioned above with respect to FIGS. 3A-B, deflects towards and away from the top substrate 232 to close and open the valve, respectively.

In certain methods of fabrication, the top substrate 232 and the membrane 238 are laminated together, and similarly the membrane 238 and the bottom substrate 230 are laminated together. While any lamination method known in the art may be used, in one aspect of the invention these layers are laminated by: 1) using a weak solvent bonding agent, and 2) laminating the layers under mild conditions, such as under low heat or low pressure. This is beneficial at least in part because this lamination method reduces or eliminates damage to the microfeatures during the lamination process. More particularly, in an exemplary use, the weak solvent bonding agent is applied to one or both surfaces to be adhered, and then mild pressure (e.g., from moderate heat or moderate physical pressure pressing the surfaces together) adheres the surfaces.

According to an aspect, the weak solvent bonding agent may be chemically defined as:

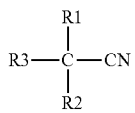

where, R1=H, OH or R, where R=alkyl, or is absent, R2=H, OH or R, where R=alkyl, or is absent, and R2=H, OH or R, where R=alkyl, or is absent.

Alternatively, the weak solvent may have a chemical formula of:

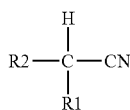

where R1=H, OH or R, where R=alkyl, or is absent, and R2=H, OH or R, where R=alkyl, or is absent.

Alternatively, the weak solvent may have a chemical formula of:

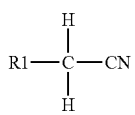

where R1=H, OH or R, where R=alkyl, or is absent.

In a particular aspect, the weak solvent bonding agent is acetonitrile. Acetonitrile is a versatile solvent that is widely used in analytical chemistry and other applications. It is 100% miscible with water and exhibits excellent optical properties. The ability of acetonitrile to have little or no effect on polymeric surfaces under ambient conditions but adhere the surfaces under moderate pressure makes it highly suitable for laminating polymeric materials such as polystyrene, polycarbonate, acrylic and other linear polymers. For example, microstructures disposed on a polystyrene substrate that was treated with acetonitrile at room temperature for at least several minutes did not exhibit any noticeable feature damage.

While some materials may be more susceptible to damage from acetonytrile than polystyrene, this increased susceptibility can be controlled by applying the acetonitrile at a lower temperature or, alternatively, by using a combination of acetonitrile and other inert solvents.

An additional benefit of acetonitrile-based lamination is that the process allows substrate alignment for structures containing multi-component layers or fluid networks constructed utilizing both a cover plate and a base plate. Unlike conventional strong solvent lamination, which tends to penetrate the polymeric surface and create a tacky bonding surface within seconds of solvent application, acetonitrile at room temperature can gently soften the surface. When two surfaces with acetonitrile disposed thereon are placed in contact at lower temperature prior to applying pressure, an operator can slide the two surfaces against each other to adjust their alignment. After aligning the surfaces, the operator can then apply pressure to the surfaces to laminate them together.

The top substrate 232, the bottom substrate 230, or the diaphragm 238 may include shallow microfeatures which may interfere with the bonding. More particularly, the bottom substrate 230 may include microfeatures having a depth on the order of about 5 μm or less, and a lateral width of more than about 1 mm. Since the membrane 238 may be deformable, any pressure applied to the surfaces during the bonding process may deflect the membrane 238 into the shallow microfeature and inadvertently bond the membrane 238 to the bottom of the microfeature. In order to prevent this, certain exemplary fabrication methods include selectively applying the weak solvent bonding agent so that the bonding agent is not present in areas where bonding should not occur.

As disclosed above, the acetonitrile bonding agent may require thermal activation to create a bond between the polymeric components. The heating can be provided in a number of ways. When the heat is applied to the components by positioning them on a heat source, the heat must be conducted through the components to the bonding interface.

Another method is referred to herein as solvent-assisted microwave bonding. In this method the substrate components are prepared for bonding as previously disclosed. However, instead of heating the bulk structure by contacting a high temperature source, the assembled component pair is exposed to microwave energy. The microwaves energy is predominately absorbed by the polar solvent molecules without affecting the bulk plastic component structure, thus heating the bonding interface without bulk heating of the substrates. This method is particularly useful in situations where the heating area needs to be surface restricted. Alternatively, the structure to be bonded or laminated by the weak solvent bonding agent may be cooled prior to weak solvent application. Specifically, acetonitrile solvent lamination and bonding can be used to fabricate diaphragms that can be used as valve and pump structures.

We claim:

1. A microfluidic system, comprising:
   a modular pneumatic manifold having a plurality of apertures that provide a passage of a pneumatic signal there through;
   a plurality of modular microfluidic chips each having different respective configurations of microfeatures, diaphragm valves, and pressure-actuatable membranes that are actuated by the pneumatic signal disposed in relation to only a single surface of each microfluidic chip; and
   a respective plurality of separate, modular chip manifolds corresponding to the plurality of microfluidic chips having pneumatic-only channels disposed therein for routing the pneumatic signal from at least some of the apertures of the pneumatic manifold to at least some of the pressure-actuatable membranes on corresponding ones of the microfluidic chips, wherein the channels route the pneumatic signal in accordance with a configuration of the plurality of pressure-actuatable membranes in the microfluidic chip wherein the respective plurality of separate, modular chip manifolds are each disposed in-between and in direct contact with the respective modular microfluidic chips and the modular pneumatic manifold, and the microfluidic system is a reconfigurable system due to the modular microfluidic chips, the separate, modular replaceable chip manifolds, and the separate, modular pneumatic manifold.

2. The system of claim 1, wherein the pneumatic signals are routed to at least one signal line in at least one of the microfluidic chips for actuating at least one sensor connected to the signal line.

3. The system of claim 1, wherein at least one of the chip manifolds includes at least one set of channels for routing a pneumatic signal from a single aperture of the pneumatic manifold to a plurality of the pressure-actuatable membranes in at least one of the microfluidic chips.

4. The system of claim 3, wherein the at least one set of channels comprises a single channel for routing the pneumatic signal from the aperture to a plurality of channels branching from the single channel, wherein the plurality of channels branching from the single channel route the pneumatic signal to respective ones of the plurality of pressure-actuatable membranes.

5. The system of claim 3, wherein the at least one set of channels includes a set consisting of a single channel.

6. The microfluidic system of claim 1, further comprising a controller for controlling the pneumatic signals being transmitted through the plurality of apertures.

7. The microfluidic system of claim 6, wherein the plurality of apertures have respective pneumatic transducers that fluidly couple to the plurality of apertures for transmitting the pneumatic signals through the plurality of apertures, and the controller is adapted to transmit electronic signals that individually actuate the respective pneumatic transducers in a sequence according to logic instructions from the controller.

8. The microfluidic system of claim 7, wherein the pneumatic transducers comprise solenoids.

9. The microfluidic system of claim 7, wherein at least one of the pneumatic transducers includes:
an output port for transmitting a pneumatic pressure, and
a switch for selecting the pneumatic pressure as one of a positive pressure and a negative pressure based on at least one of the electronic signals.

10. The microfluidic system of claim 9, wherein the pneumatic pressure is generated by a diaphragm pump coupled to the output port, further wherein the diaphragm pump is DC-powered and has a size that facilitates portability of the microfluidic system.

11. The microfluidic system of claim 1, wherein the pneumatic manifold includes a plurality of laminated layers.

12. The microfluidic system of claim 1, wherein the pneumatic manifold further comprises attachment ports for coupling pneumatic transducers to the pneumatic manifold.

13. The microfluidic system of claim 1, wherein the plurality of apertures have respective pneumatic transducers that fluidly couple to the plurality of apertures, the pneumatic manifold includes at least one positive pressure source and at least one negative pressure source, and the at least one positive pressure source and the at least one negative pressure source fluidly couple to the pneumatic transducers.

14. The microfluidic system of claim 13, wherein the at least one positive pressure source provides signals corresponding to a first state of binary logic communicated to the pneumatic transducers from a controller, and the at least one negative pressure source provides signals corresponding to a second state of binary logic communicated from a controller to the pneumatic transducers.

15. The microfluidic system of claim 1, wherein the plurality of microfluidic chips include at least one microfluidic pump, and the microfluidic pump includes three or more of the plurality of pressure-actuatable membranes.

16. The microfluidic system of claim 1, wherein the plurality of microfluidic chips include a plurality of fluidic assay channels for transporting and reacting fluidic reagents.

17. The microfluidic system of claim 1, wherein the plurality of microfluidic chips include a plurality of reagent reservoirs for storing fluidic reagents, and a plurality of outlet reservoirs for storing reaction products of the fluidic reagents.

18. The microfluidic system of claim 1, further comprising an optical detection system for analyzing fluidic samples in the plurality of microfluidic chips.

19. The microfluidic system of claim 18, wherein the optical detection system includes a light source for transmitting light through the fluidic samples, and a transducer for receiving at least a portion of the transmitted light and producing an electronic signal related to the strength of the received portion of the transmitted light.

20. The microfluidic system of claim 19, wherein the optical detection system further includes a slit disposed between the light source and the transducer for attenuating ambient light.

21. The microfluidic system of claim 19, wherein the optical detection system further includes a band-pass filter disposed between the light source and the transducer.

22. The microfluidic system of claim 19, wherein the optical detection system further includes an automated calibration system for calibrating a plurality of the transducers.

23. The microfluidic system of claim 1, wherein each of the pneumatic manifold, the plurality of chip manifolds, and the plurality of microfluidic chips comprise a non-elastomer plastic material.

24. The microfluidic system of claim 23, wherein the non-elastomer plastic material comprises at least one of polymethyl methacrylate, polystyrene, polycarbonate, and acrylic.

* * * * *